US008058027B2

(12) United States Patent
DiLeo

(10) Patent No.: US 8,058,027 B2
(45) Date of Patent: Nov. 15, 2011

(54) CELL CULTURE METHODS FOR PRODUCING RECOMBINANT PROTEINS IN THE PRESENCE OF REDUCED LEVELS OF ONE OR MORE CONTAMINANTS

(75) Inventor: Anthony DiLeo, Westford, MA (US)

(73) Assignee: Millipore Corporation, Billerica, MA (US)

( * ) Notice: Subject to any disclaimer, the term of this patent is extended or adjusted under 35 U.S.C. 154(b) by 644 days.

(21) Appl. No.: 12/006,984

(22) Filed: Jan. 8, 2008

(65) Prior Publication Data

US 2009/0181426 A1    Jul. 16, 2009

Related U.S. Application Data

(60) Provisional application No. 60/879,221, filed on Jan. 8, 2007.

(51) Int. Cl.
*C12P 21/06* (2006.01)
*C12P 21/04* (2006.01)
(52) U.S. Cl. .................................. 435/69.1; 435/70.1
(58) Field of Classification Search .................. None
See application file for complete search history.

(56) References Cited

U.S. PATENT DOCUMENTS

| 5,583,009 A | 12/1996 | Palmiter et al. |
| 5,610,053 A | 3/1997 | Chung et al. |
| 6,689,606 B2 | 2/2004 | Antoniou et al. |
| 6,881,556 B2 | 4/2005 | Antoniou et al. |
| 6,949,361 B2 | 9/2005 | Antoniou et al. |
| 6,964,951 B2 | 11/2005 | Antoniou et al. |
| 7,129,062 B2 | 10/2006 | Mermond |
| 7,442,787 B2 | 10/2008 | Antoniou et al. |

FOREIGN PATENT DOCUMENTS

| WO | WO94/13273 | | 6/1994 |
| WO | WO95/33841 | | 12/1995 |
| WO | WO98/07876 | | 2/1998 |
| WO | WO00/05393 | | 2/2000 |
| WO | WO/2005/065348 | * | 7/2005 |
| WO | WO2005/065348 | | 7/2005 |
| WO | WO2008/134200 | | 11/2008 |

OTHER PUBLICATIONS

Figueroa et al., Enhanced cell culture performance using inducible anti-apoptotic genes E1B-19K and Aven in the production of a monoclonal antibody with Chinese hamster ovary cells, Biotechnology and Bioengineering, E. pub. Nov. 10, 2006, vol. 97, pp. 877-892.*
Ohyama et al., Optimized conditions for gene transfection into the human eosinophilic cell line EoL-1 by electroporation, Journal of Immunological Methods,1998, vol. 215, pp. 105-111.*
Picture of electroporation cuvettes (last viewed on Aug. 13, 2010).*
Catzel et al., Purification of recombinant human growth hormone from CHO cell culture supernatant by Gradiflow preparative electrophoresis technology, Protein Expression and Purification, Nov. 2003, vol. 32, Issue 1, pp. 126-134.*
Williams et al., CpG—island fragments from the HNRPA2B1/CBX3 genomic locus reduce silencing and enhance transgene expression from the hCMV promoter/enhancer in mammalian cells., BMC Biotechnology, Jun. 3, 2005, vol. 5:17, pp. 1-9.*
Peter Gunning et al., A human β-actin expression vector system directs high-level accumulation of antisense transcripts, Proc. Natl. Acad. Sci, vol. 84, pp. 4831-4835, Jul. 1987.
M. Garidiner-Garden et al., CpG Islands in Vertebrate Genomes, J. Mol. Biol. 196, 261-282, 1987.
Bonifer, "Long-distance chromatin mechanisms controlling tissue-specific gene locus activation", Gene, 238(2):277-289, Oct. 1999.
Anderson, "Human gene therapy", Nature, 392(Supp):25-30, Apr. 1998.
Verma et al., "Gene therapy-promises, problems and prospects", Nature, 389:239-242, Sep. 1997.
Corcoran et al., "High-level regulated expression of the human G6PD gene in transgenic mice", Gene, 173(2):241-246, Sep. 1996.
Biamonti et al., "Two homologous genes, originated by duplication, encode the human hnRNP proteins A2 and A1", Nucl. Acids Res., 22(11):1996-2002, Jun. 1994.
Genbank Accession No. U09120, National Library of Medicine, accessed by PTO, Jul. 5, 2000, Dec. 1994.
Genbank Accession No. D28877, National Library of Medicine, accessed by PTO, Jul. 5, 2000, Feb. 1999.
Genbank Accession No. AL031259, version AL031259.7 GI:3676176, accessed by PTO, Jul. 13, 2000, Sep. 1998.
Chalut et al., "Genomic structure of the human TATA-box-binding protein (TBP)", Gene, 161 (2):277-282, Aug. 1995.
Foulds et al., "Analysis of the human TATA binding protein promoter and identification of an Ets site critica for activity", Nucl. Acids Res., 25(12):2485-2494, Jun. 1997.
Li et al, "Locus control regions: coming of age at a decade plus", Trends in Genetics, 15(10):403-408, Oct. 1999.
Chung et. al.; Characterization of the chicken β-globin insulator, 1997, Proc. Natl. Acad. Sci. vol. 94: 575-580.
Crane-Robinson, C. et al., "Chromosomal mapping of core histone acetylation by immunoselection," Methods, 1997, 12(1), 48-56 (summary only).
DiBartolomeis, S.M. et al., "A superfamily of *Drosophila* satellite related (SR) DNA repeats restricted to the X chromosome euchromatin," Nucl. Acids Res., 1992, 20(5), 1113-1116.
Duhig, T. et al., "The Human Surfeit Locus," Genomics, 1998, 52, 72-78.
Ellis, J. et al., "A dominant chromatin-opening activity in 5' hypersensitive site 3 of the human β-globin locus control region," EMBO J., 1996, 15(3), 562-568.
Ellis, J. et al., "Evaluation of β-globin gene therapy constructs in single copy transgenic mice," Nucl. Acids Res., 1997, 26(6), 1296-1302.
Gaston, K. et al., "CpG methylation has differential effects on the binding of YY1 and ETS proteins to the bi-directional promotor of the Surf-1 and Surf-2 genes," Nucl. Acids Res., 1995, 23(6), 901-909.
Gaston, K. et al., "YY1 is involved in the regulation of the bi-directional promoter of the Surf-1 and Surf-2 genes," FEBS Letts., 1994, 347, 289-294.

(Continued)

*Primary Examiner* — Alexander Kim

(57) ABSTRACT

The invention relates to cell culture methods, kits and cell lines for producing recombinant products, e.g. therapeutic proteins and antibodies, in the presence of reduced levels of one or more contaminants and further to methods of purifying those products.

29 Claims, No Drawings

OTHER PUBLICATIONS

Garson, K. at al., "Surf5: A Gene in the Tightly Clustered Mouse Surfeit Locus is Highly Conserved and Transcribed Divergently from the rpL7a (Surf 3) Gene," Genomics, 1996, 30, 163-170.

Gavalas, A. et al., "Analysis of the chicken GPAT/AIRC bidirectional promoter for de novo purine nucleotide synthesis," J. Biol. Chem., 1995, 270(5), 2403-2410.

Lavia, P. et al., "Coincident start sites for divergent transcripts at a randomly selected CpG-rich island of mouse," EMBO J., 1987, 6, 2773-2779.

Ortiz, B.D. et al., "Adjacent DNA elements dominantly restrict the ubiquitous activity of a novel chromatin-opening region to specific tissues," EMBO J., 1997, 16, 5037-5045.

Palmiter, "The elusive function of metallothioneins," Proc. Natl. Acad. Sci. USA, 1998, 95, 8428-8430.

Talbot, D. et al., "The 5' flanking region of the rat LAP (C/EBPβ) gene can direct high-level, position-independent, copy number-dependent expression in multiple tissues in transgenic mice," Nucl. Acids Res., 1994, 22(5), 756-766.

Williams, T.J. et al., "The MES-1 Murine Enhancer Element is Closely Associated with the Heterogeneous 5' Ends of Two Divergent Transcription Units," Mol. Cell. Biol., 1986, 6(12), 4558-4569.

Winston, J. H. et al., "An intron 1 regulatory region from the murine adenosine deaminase gene can activate heterologous promoters for ubiquitous expression in transgenic mice," Som. Cell Mol. Genet., 1996, 22, 261-278.

Festenstein, R., et al., "Locus control region function and heterochromatic-induced position effect variegation," Science, 1996, 271(23), 1123-1125.

Gavalas, A., et al., "Coexpression of two closely linked avian genes for purine nucleotide synthesis from a bidirectional promoter," Mol. Cell Biol., 1983, 13(8), 4784-4792.

Huxley, C., et al., "The mouse surfeit locus contains a cluster of six genes associated with four Gp G-rich islands in 32 kilobases of genomic DNA," Mol. Cell Biol., 1990, 10(2), 605-614.

Ohbayashi, T., et al., "Promoter structure of the mouse TATA-binding protein (TBP) gene," Biochem. Biophys. Res. Commun., 1996, 225(1), 275-280.

Ryan M.T., et al., "The genes encoding mammalian chaperonin 60 and chaperonin 10 are linked head-to-head and share a bidirectional promoter," Gene: An International J on Genes and Genomes, 1997, 196(1-2), 9-17.

Ursini, et al., 1990, High levels of transcription driven by a 400 by segment of the human G6PD promotor, Biochem. Biophys. Res. Commun., 170:1203-1209.

Shewchuk and Hardison, "CpG Islands from the α-Globin Gene Cluster Increase Gene Expression in an Integration-Dependend Manner," Molecular and Cellular Biology. Oct. 1997, 17(10):5856-5866.

Larsen, F. et al., "CpG Islands as Gene Markers in the Human Genome," Genomics, 1992, 13:1095-1107.

Pikaart, Michael J., "Loss of transcriptional activity of a transgene is accompanied by DNA methylation and histone deacetylation and is prevented by insulators," Genes and Development, 1998, 12:2852-2862.

Recillas-Targa, F. et al., "Positional enhancer-blocking activity of the chicken β-globin insulator in tranciently transfected cells," Proc. Natl. Acad. Sci. USA, 1999, 96(25):14354-14359.

Ng et al., "Evolution of the Functional Human β-Actin Gene and Its MultiPseudogene Family: Conservation of Noncoding Regions and Chromosomal Dispersion of Pseudogenes," Mol. Cell. Biol., vol. 5, 1985, pp. 2720-2732.

Antequera, F. & Bird, A., "Number of CpG islands and genes in human and mouse" Proc. Natl. Acad. Sci. USA, 1993, 90, 11995-11999.

Bell, A.C. & Felsenfield, G., "Stopped at the border: boundaries and insulators" Curr. Opin. Genet. Dev.,1999, 9, 191-198.

Bird et al., A fraction of the mouse genome that is derived from islands of nonmethylated, CpG-rich DNA, Cell, 1985, 40:91-99.

Dillon, N. & Grosveld, F., "Chromatin domains as potential units of eukaryotic gene function" Curr. Opin. Genet. Dev., 1994, 4, 260-264.

Hammer, et al., "Production of transgenic rabbits, sheep and pigs by microinjection" Nature, 1985, 315:680-683.

Hicks, et al., "Functional genomics in mice by tagged sequence mutagenesis" Nature Genetics, 1997, 16, 338-344.

Kioussis, D. & Festenstein, R., "Locus control regions: overcoming heterochromatin-induced gene inactivation in mammals" Curr. Opin. Genet. Dev.,1997, 7, 614-619.

Needham, et al., "Further development of the locus control region/ murine erthroleukemia expression system: high level expression and characterization of recombinant human calcitonin receptor" Protein Expr. Purif., 1995, 6:124-131.

Sabbattini, P., Georgiou, A., Sinclaire, C. & Dillon, N., "Analysis of mice with single and multiple copies of transgenes reveals a novel arrangement for the .lambda.5-V-preBI locus control region" Mol. Cell. Biol, 1999,19, 671-679.

Tazi, J. & Bird, A., "Alternative chromatin structure at CpG islands",Cell 60,1990, 909-920.

Cavazzana-Calvo, M., et al., "Gene Therapy of Human Severe Combined Immunodeficiency (SCID)-X1 Disease," Science, 288:669-672, (2000).

Cheng, L., et al., "A GFP reporter system to assess gene transfer and expression in human hematopoietic progenitor cells," Gene Therapy, 4:1013-1022, (1997).

Cheng, L., et al., "Sustained Gene Expression in Retrovirally Transduced, Engrafting Human Hematopoietic Stem Cells and Their Lympho-Myeloid Progeny," Blood, 92(1):83-92, (Jul. 1, 1998).

Elwood, N.J., et al., "Retroviral Transduction of Human Progenitor Cells: Use of Granulocye Colony-Stimulating Factor Plus Stem Cell Factor to Mobilize Progenitor Cells In Vivo and Stimulation by Flt3/Flk-2 Ligand In Vitro," Blood, 88(12):4452-4462, (Dec. 15, 1996).

Lu, L., et al., "High Efficiency Retroviral Mediated Gene Trnasduction into Single Isolated Immature and Replatable CD34.sup.3+ Hematopoietic Stem/Progenitor Cells from Human Umbilical Cord Blood," J. Exp. Med., 178:2089-2096, (Dec. 1993).

Whitwam, T., et al., "Retroviral Marking of Canine Bone Marrow: Long-Term, High-Level Expression of Human Interleukin-2 Receptor Common Gamma Chain in Canine Lymphocytes," Blood, 92(5):1565-1575, (Sep. 1, 1998).

Webpage, the National Institutes for Health for Severe Combined Immunodeficiency ("SCID") in 1990.

Hardison, R., "Hemoglobins from Bacteria to Man: Evolution of Different Patterns of Gene Expression," J. of Experimental Biology 201, 1099-1117 (Mar. 1998), Cambridge, UK.

Juengst, "What next for human gene therapy," Brit. Med. J., vol. 326, pp. 1410-1411, Jun. 28, 2003.

Klehr, D. et al. "Scaffold-Attached Regions From the Human Interferon Beta Domain Can Be Used to Enhance the Stable Expression of Genes Under the Control of Various Promoters", Biochemistry, American Chemical Society, 30(5), 1264-1270, Feb. 5, 1991.

Williams Steven et al., "CpG—island fragments from the HNRPA2B1/CBX3 genomic locus reduce silencing enhance transgene expression from the hCMV promoter/enhancer in mammalian cells" BMC Biotechnology. Biomed Central LTD, 5(1) 1472-6750, Jun. 3, 2005.

Darrin Kuystermans et al., "Using cell engineering and omic tools for the improvement of cell culture processes", Cytotechnology, Kluwer Acedemic Publishers, DO, 53(1-3) 3-22, Feb. 24, 2007.

PCT/US2008/000244, International Search Report, Jul. 20, 2008.

PCT/US2008/000230, International Search Report, Jul. 8, 2008.

Coffinier, Y. et al. "Separation of IgG fromhuman plasma using thiophilic hollow fiber membranes" Journal of Membrane Science, Elsevier Science Publ. Co., 208(1-2), 13-22, Oct. 1, 2002.

Schwartz, W. et al. "Comparison of hydrophobic charge induction chromatography with affinity chromatography on protein A for harvest and purification of antibodies" Journal of Chromatography, Elsevier Science Publishers, 908(1-2), 251-263, Jan. 26, 2001.

Przybycien, T M, et al. "Alternative bioseparation operations: life beyond packed-bed chromatography" Current Opinion in Biotechnology, 15(5), 469-478, Oct. 1, 2004.

Lightfoot, E N., et al. "Bioseparations" Biotechnology and Bioengineering, Wiley & Sons, 87(3), 259-273, Jul. 7, 2004.

Christy, C., et al. "High-performance tangential flow filtration: a highly selective membrane separationprocess" Desalination, Elsevier, 144(1-3), 133-136, Sep. 10, 2002.

Mahler, SM., et al. "Purification of monoclonal antibodies from cell culture supernatants by Gradiflow(TM) electrophoresis technology" Journal of Chemical Technology and Biotechnology, 81(3), 445-453, Mar. 3, 2006.

Nivitchanyong, T., et al., "Anti-apoptotic Genes Aven adn E1B-19K Enhance Performance BHK Cells Engineered to Express Recombinant Factor VIII in Batch and Low Perfusion Cell Culture" Biotechnology & Bioengeneering, pp. 825-841, E. pub. May 18, 2007.

Mollet, M., et al., "Acute Hydrodynamic Forces and Apopotosis: A complex question" Biotechnology & Bioengineering, 98(4) 772-788, Nov. 1, 2007.

* cited by examiner

US 8,058,027 B2

CELL CULTURE METHODS FOR PRODUCING RECOMBINANT PROTEINS IN THE PRESENCE OF REDUCED LEVELS OF ONE OR MORE CONTAMINANTS

RELATED APPLICATIONS

This application claims the benefit of priority of U.S. Provisional Patent Application No. 60/897,221, filed on Jan. 8, 2007, the entire contents of which are incorporated by reference herein.

This application is related to U.S. Provisional Patent Application No. 60/872,162, also filed on Jan. 8, 2007, and U.S. patent application Ser. No. 12/006,960, filed on Jan. 8, 2008, and entitled "High Expression Cell Line That Eliminates Gene Amplification" the entire contents of each of which are incorporated by reference herein.

The entire contents of each of these patent applications are hereby expressly incorporated herein by reference including without limitation the specification, claims, and abstract, as well as any figures, tables, or drawings thereof.

FIELD OF THE INVENTION

The invention relates generally to the field of recombinant protein expression technology. More specifically, the present invention provides methods, cell lines, and kits for enriching for recombinant proteins in cell culture as well as methods of purifying such proteins.

BACKGROUND OF THE INVENTION

The advent of recombinant technology, allowing the production of recombinant proteins in desirable host cells, has opened the door to various uses for recombinantly produced proteins. Production of recombinant proteins suitable for use as therapeutics, diagnostic and/or research reagents is widely known within the biotechnology field. Notably, over the past decade, therapeutic proteins have become increasingly prominent. Typically, the process for producing a recombinant protein ranges from identifying a clone which produces a desirable product, to scaling up manufacturing and product purification and usually is arduous and lengthy, demanding a significant commitment of time, labor and resources. With recombinant proteins becoming entrenched in the therapeutics market, more efficient ways of producing and purifying recombinant products is desirable. However, merely increasing production of a recombinant protein is not sufficient. For example, most recombinantly produced proteins are present in complex mixtures of products, which makes the task of purifying the desired recombinant protein challenging as well as time consuming. Furthermore, due to the strict Federal Food and Drug Administration requirements on protein consistency, quality, and purity, better methods of protein production and purification are desired.

Accordingly, there is a need for improved technologies which result in higher quantities as well as improved quality of the protein produced.

SUMMARY OF THE INVENTION

The present invention provides methods for enriching for a recombinant protein in cell culture, for example, by reducing the levels of one or more contaminants. In certain embodiments, the invention relates to improved methods, kits and cell lines for the recombinant production of proteins. The invention thus provides, in some embodiments, methods that are simpler to perform, more efficient and less expensive than previously described methods suitable for the production of a recombinant protein. Still other embodiments of the present invention provide a stably transfected cell line which is easier to make, easier to grow and less expensive to maintain than previously described stably transfected cell lines for the production of recombinant proteins. Yet other embodiments of the invention provide a method of harvesting a recombinant protein from a cell culture that is faster, simpler, safer, and more effective. Proteins as used herein include full length proteins, protein domains, protein fragments, polypeptides and peptides comprising two or more amino acids. In some embodiments, recombinant proteins expressed using the methods of the present invention are therapeutic proteins. In yet other embodiments, recombinant proteins expressed using the methods of the present invention are antibodies or antigen binding fragments thereof.

In some embodiments according to the present invention, a method of enriching for a recombinant protein in cell culture is provided. The method comprises: (a) introducing into a cell, a first nucleic acid molecule comprising a nucleotide sequence encoding a recombinant protein and a second nucleic acid molecule comprising a nucleotide sequence encoding at least one anti-apoptotic protein or a functional fragment thereof, where both nucleotide sequences are operably linked to one or more DNA elements capable of opening chromatin and/or maintaining the chromatin in an open state; and (b) culturing the cell under conditions such that the recombinant protein is produced in the presence of reduced levels of one or more contaminants, thereby to enrich for the recombinant protein in cell culture. In some embodiments, such a method further comprises the step of harvesting the recombinant protein from cell culture, where the recombinant protein is produced in the presence of reduced levels of one or more contaminants.

In some embodiments, a cell containing a nucleotide sequence encoding an apoptotic protein or a functional fragment thereof is further transfected with a nucleic acid molecule comprising a nucleotide sequence encoding a recombinant protein operably linked to a nucleotide sequence capable of opening chromatin and/or maintaining chromatin in an open state and is cultured under conditions to produce the recombinant protein in the presence of reduced levels of one or more contaminants.

The one or more contaminants include, but are not limited to, one or more host cell lipids, one or more host cell proteins, one or more host cell carbohydrates, one or more host cell RNA molecules and one or more host cell DNA molecules. In a particular embodiment, a recombinant protein is produced in the presence of reduced levels of one or more host cell proteins, where the one or more host cell proteins are present in an amount less than 1000 ppm, or less than 900 ppm, or less than 800 ppm, or less than 700 ppm, or less than 600 ppm, or less than 500 ppm, or less than 400 ppm, or less than 300 ppm, or less than 200 ppm, or less than 100 ppm, or less than 75 ppm, or less than 50 ppm, or less than 25 ppm, or less than 10 ppm, or less than 5 ppm, or less than 3 ppm, or less than 1 ppm of the total protein. Host cell contaminants, e.g., host cell proteins, can be readily measured using one or more assays known in the art and those commercially available (e.g., from Cygnus Technologies, Inc).

The levels of the one or more contaminants may be reduced by any statistically significant amount when a recombinant protein is co-expressed with an anti-apoptotic protein or functional fragment thereof using a DNA element capable of opening chromatin and/or maintaining chromatin in an open state, relative to the levels when the recombinant protein is expressed alone. In some embodiments, the levels of one or more contaminants are reduced by about 20%, or about 30%, or about 40%, or about 50%, or about 60%, or about 70%, or about 80%, or about 90%, or about 95%, or about 96%, or about 97%, or about 98%, or about 99%, or more, when the recombinant protein and the anti-apoptotic protein or functional fragment thereof are co-expressed relative to the levels of one or more contaminants present when the recombinant protein is expressed alone.

In one embodiment, a host cell is first transfected with a nucleic acid molecule comprising a nucleotide sequence encoding an anti-apoptotic protein or a functional fragment thereof followed by transfection with a nucleic acid molecule comprising a nucleotide sequence which encodes a recombinant protein.

In another embodiment, a host cell is transfected with both nucleic acid molecules at the same time.

The first nucleic molecule and the second nucleic acid molecule may be cloned into the same vector or into separate vectors. In some embodiments, the vector is a plasmid. In other embodiments, the vector is a viral vector.

In some embodiments, the first nucleic acid molecule comprises two nucleotide sequences, each encoding a recombinant protein, and each operably linked to one or more DNA elements capable of opening chromatin and/or maintaining chromatin in an open state. In a particular embodiment, the first nucleic acid molecule includes two nucleotides sequences, one encoding for the light chain of an antibody and the other encoding for the heavy chain of an antibody.

In some embodiments, the recombinant protein is a therapeutic protein. In other embodiments, the recombinant protein is an antibody or an antigen-binding fragment thereof. In some embodiments, the antibody is a monoclonal antibody.

In some embodiments, the first nucleic acid molecule further comprises one or more nucleotide sequences chosen from: (a) a nucleotide sequence capable of enhancing translation; (b) a nucleotide sequence capable of increasing secretion; and (c) a nucleotide sequence capable of increasing the mRNA stability, where the one or more nucleotide sequences set forth in (a)-(c) are operably linked to the nucleotide sequence encoding the recombinant protein.

In some embodiments, the cell is a mammalian cell such as, for example, a BHK21 cell, a CHO cell, a CHO-K1 cell, a CHO-DUXX cell, an NSO cell or an Sp2/0 cell. In some embodiments, the mammalian cell is a Chinese Hamster Ovary Cell (CHO cell).

In some embodiments, the one or more DNA elements capable of opening chromatin and/or maintaining the chromatin in an open state are chosen from: (a) one or more an extended methylation-free CpG islands; (b) one or more matrix attachment regions; (c) one or more stabilizing and antirepressor regions; and (d) any combinations of (a)-(c). In some embodiments, the one or more extended methylation-free CpG islands are derived from the promoter region of one or more ubiquitously expressed genes. Exemplary ubiquitously expressed genes include, but are not limited to, human hnRNPA2 gene, rat hnRNPA2 gene, mouse hnRNPA2 gene, human TBP gene, mouse TBP gene, human rpS3 gene and mouse rpS3 gene. Sequences of exemplary extended methylation-free CpG islands which may be used in the methods, kits and cell lines described herein are set forth in SEQ ID NO:1, which depicts a 3.2 kb fragment derived from the promoter region of the mouse rpS3 gene (Genbank Accession Nos. AY999160 and AY043296) and SEQ ID NO:2, which depicts a 1.5 kb fragment derived from the promoter region of the human hnRNPA2 gene (Genbank Accession No. D28877). Additionally, larger fragments derived from the human hnRNPA2 gene set forth in SEQ ID NO:3 (4 kb sequence) and SEQ ID NO:4 (8 kb sequence) can also be used in the methods of the invention.

In some embodiments, the one or more DNA elements capable of opening chromatin and/or maintaining chromatin in an open state are naturally occurring DNA elements. In other embodiments, the one or more DNA elements capable of opening chromatin and/or maintaining chromatin in an open state are artificially synthesized DNA elements. In yet other embodiments, the one or more DNA elements capable of opening chromatin and/or maintaining chromatin in an open state are a combination of naturally occurring and artificially synthesized DNA elements.

In some embodiments, the nucleotide sequence encoding the anti-apoptotic protein is chosen from a nucleotide sequence encoding bcl-2; bcl-$x_L$; bcl-6; survivin; xiap; hiap1; hiap2; aven; E1B-19K; P21; myrPHK; HSV-1 γ1 34.5; and beclin, or a functional homolog or fragment thereof. Exemplary nucleotide sequences of anti-apoptotic genes which may be used in the methods of the invention are set forth in SEQ ID NO:5 and SEQ ID NO:7, which represent human and mouse nucleotide sequences for the anti-apoptotic gene, aven, respectively, and SEQ ID NO:9, which represents the nucleotide sequence of the human E1B-19K gene. It is understood that variants and fragments of these sequences may also be used, so long as they exhibit one or more functional activities associated with the respective anti-apoptotic protein. Alternatively, cells maybe contacted with purified or isolated anti-apoptotic proteins or fragments thereof. Exemplary amino acid sequences of anti-apoptotic proteins are set forth in SEQ ID NOs:6, 8 and 10.

In some embodiments, the cells used for producing a recombinant protein are cultured in a serum free medium. In some embodiments, the medium is free of animal products. In other embodiments, the medium is free of protein.

In some embodiments, the first and/or the second nucleic acid molecules are introduced into a host cell by: (a) placing the host cell in an electroporation device comprising a barrier having an opening suitable for receiving the host cell; (b) securing the host cell in the opening; (c) contacting the host cell with an electric current such that the current passes through the host cell; (d) monitoring the ratio between the current and voltage in the electroporation device; and (e) adjusting the magnitude of the voltage to optimize electroporation.

Also provided are kits for producing a recombinant protein in the presence of reduced levels of one or more contaminants. In some embodiments, a kit according to the invention comprises: (a) a first nucleic acid molecule comprising one or more DNA elements capable of opening chromatin and/or maintaining chromatin in an open state and a multiple cloning site suitable for cloning a nucleotide sequence encoding the recombinant protein; and (b) a second nucleic acid molecule comprising a nucleotide sequence encoding at least one anti-apoptotic protein or a functional fragment thereof operably linked to one or more DNA elements capable of opening chromatin and/or maintaining chromatin in an open state. In some embodiments, a kit according to the invention further comprises one or more of a cell line comprising a plurality of host cells suitable for introduction of the first and/or the second nucleic acid molecules and a transfection reagent or a transfection device along with instructions for using the transfection reagent or device, e.g., an electroporation device as described herein.

In some embodiments, a kit according to the invention is used for producing a therapeutic protein. In other embodiments, the kit is used for producing an antibody or an antigen-binding fragment thereof. In some embodiments, the antibody is a monoclonal antibody.

In some embodiments, the one or more DNA elements capable of opening chromatin and/or maintaining chromatin in an open state in the kits of the invention are naturally occurring DNA elements. In other embodiments, the one or more DNA elements capable of opening chromatin and/or maintaining chromatin in an open state are artificially synthesized DNA elements. In yet other embodiments, the one or more DNA elements capable of opening chromatin and/or maintaining chromatin in an open state are a combination of naturally occurring and artificially synthesized DNA elements.

In some embodiments, a kit according to the invention includes one or more nucleic acid molecules comprising one or more DNA elements capable of opening the chromatin and/or maintaining the chromatin in an open state, where such sequences are chosen from: (a) one or more an extended methylation-free CpG islands; (b) one or more matrix attachment regions; (c) one or more stabilizing and antirepressor regions; and (d) any combinations of (a)-(c). In some embodiments, the one or more extended methylation-free CpG islands are derived from the promoter region of one or more ubiquitously expressed genes.

In some embodiments, a nucleotide sequence encoding the anti-apoptotic protein in the kits according to the invention is chosen from a nucleotide sequence encoding bcl-2; bcl-$x_L$; bcl-6; aven; survivin; xiap; hiap1; hiap2; E1B-19K; P21; myrPHK; HSV-1 γ1 34.5; and beclin, or a functional fragment or homolog thereof.

The present invention further provides a host cell suitable for producing a recombinant protein in the presence of reduced levels of one or more contaminants. In some embodiments, a host cell comprises: (a) a nucleic acid molecule comprising a nucleotide sequence encoding a recombinant protein operably linked to one or more DNA elements capable of opening chromatin and/or maintaining chromatin in an open state; and (b) a nucleic acid molecule comprising a nucleotide sequence encoding at least one anti-apoptotic protein or a functional fragment thereof operably linked to one or more DNA elements capable of opening chromatin and/or maintaining chromatin in an open state.

In some embodiments, a host cell includes one or more DNA elements capable of opening chromatin and/or maintaining chromatin in an open state, which are naturally occurring DNA elements. In other embodiments, the one or more DNA elements capable of opening chromatin and/or maintaining chromatin in an open state are artificially synthesized DNA elements. In yet other embodiments, the one or more DNA elements capable of opening chromatin and/or maintaining chromatin in an open state are a combination or naturally occurring and artificially synthesized DNA elements. In some embodiments, the one or more DNA elements capable of opening the chromatin and/or maintaining the chromatin in an open state are chosen from: (a) one or more an extended methylation-free CpG islands; (b) one or more matrix attachment regions; (c) one or more stabilizing and antirepressor regions; and (d) any combinations of (a)-(c). In some embodiments, the one or more extended methylation-free CpG islands are derived from the promoter region of one or more ubiquitously expressed genes. In some embodiments, a host cell according to the invention includes a nucleotide sequence encoding a recombinant protein operably linked to a nucleotide sequence set forth in SEQ ID NO:1 and/or SEQ ID NO:2, and a nucleotide sequence encoding an anti-apoptotic protein or functional fragment thereof, also operably linked to a nucleotide sequence set forth in SEQ ID NO:1 and/or SEQ ID NO:2., or homologs or fragments thereof.

In some embodiments, the host cells comprise a nucleotide sequence encoding an anti-apoptotic protein chosen from bcl-2; bcl-$x_L$; bcl-6; aven; survivin; xiap; hiap1; hiap2; E1B-19K; P21; myrPHK; HSV-1 γ1 34.5; and beclin, or a functional homolog or fragment thereof.

In some embodiments, a cell line according to the invention comprises a plurality of host cells described herein. Exemplary host cells include mammalian host cells, e.g., a BHK21 cell, a CHO cell, a CHO-K1 cell, a CHO-DUXX cell, an NSO cell or an Sp2/0 cell. In some embodiments, the mammalian cell is a Chinese Hamster Ovary Cell (CHO cell).

In some embodiments, a host cell further comprises one or more of: (a) a nucleotide sequence capable of enhancing translation of the recombinant protein; (b) a nucleotide sequence capable of increasing secretion of the recombinant protein outside the cell; and (c) a nucleotide sequence capable of increasing the stability of the mRNA encoding the recombinant protein.

Also encompassed by the present invention are methods of harvesting a recombinant protein produced using the methods described herein. In some embodiments, a method of harvesting a recombinant protein is provided, where such a method does not employ the use of protein A. In some embodiments, such a method employs one or more steps chosen from precipitation of the recombinant protein from a supernatant; crystallization; high performance tangential flow filtration (HPTFF), flow through chromatography; and adsorption chromatography. In some embodiments, a method of harvesting the recombinant protein according to the invention employs an adsorption chromatography step which is an ion exchange step. In some embodiments, a method of harvesting the recombinant protein does not include contacting the protein with a stringent elution buffer. In other embodiments, a method of harvesting a recombinant protein includes at least one centrifugation step.

In some embodiments, the molar ratio of a recombinant protein produced in the presence of an anti-apoptotic protein or functional fragment thereof by a host cell according to the invention to the one or more contaminants in a cell supernatant is increased by a statistically significant amount compared to a cell which expresses the recombinant protein alone. The anti-apoptotic protein or functional fragment thereof may either be expressed by stably transfecting a nucleotide sequence encoding the anti-apoptotic protein or functional fragment thereof into a host cell which also expresses the recombinant protein or such a host cell may be contacted with an isolated anti-apoptotic protein or functional fragment thereof.

DETAILED DESCRIPTION OF THE INVENTION

The present invention is based, at least in part, on the discovery that, recombinant proteins, when produced using cell culture methods, are present in a mixture with one or more contaminants such as, for example, host cell debris. Accordingly, the present invention provides methods of enriching for a recombinant protein by reducing the levels of one or more contaminants.

In various embodiments the invention provides improved methods of engineering transfected cell lines, e.g. stably transfected cell lines, to produce optimal quantities of a desired product, e.g. recombinant protein, while reducing the cost and time involved in developing, screening and purifying the product. These improvements are achieved, at least in part, by reducing the levels of one or more contaminants present during the harvesting of the cell culture for isolating a desired product.

I. DEFINITIONS

In order that the present disclosure may be more readily understood, certain terms are first defined. Additional definitions are set forth throughout the detailed description.

The terms "cell," "cells," "host cell," and "host cells," as used herein, encompass animal cells and include invertebrate, non-mammalian vertebrate and mammalian cells. Exemplary non-mammalian vertebrate cells include, for example, avian cells, reptilian cells and amphibian cells. Exemplary invertebrate cells include, but are not limited to, insect cells such as, for example, caterpillar (*Spodoptera frugiperda*) cells, mosquito (*Aedes aegypti*) cells, fruitfly (*Drosophila melanogaster*) cells, Schneider cells, and *Bombyx mori* cells. See, e.g., Luckow et al., Bio/Technology 6:47-55 (1988). The cells may be differentiated, partially differentiated or undifferentiated, e.g. stem cells, including embryonic stem cells and hematopoietic stem cells. Additionally tissue samples derived from organs or organ systems may be used according to the invention.

Exemplary mammalian cells include, for example, cells derived from human, non-human primate, cat, dog, sheep, goat, cow, horse, pig, rabbit, rodents including mouse, hamster, rat and guinea pig and include, but are not limited to, BHK21 cells, CHO cells, NSO cells, Sp2/o cells, and any derivatives and progenies thereof.

Additionally, hybridoma cells can also be used in the methods of the invention. The term "hybridoma" refers to a hybrid cell line produced by the fusion of an immortal cell line of immunologic origin and an antibody producing cell. The term encompasses progeny of heterohybrid myeloma fusions, which are the result of a fusion with human cells and a murine myeloma cell line subsequently fused with a plasma cell, commonly known as a trioma cell line. Furthermore, the term is meant to include any immortalized hybrid cell line which produces antibodies such as, for example, quadromas. See, e.g., Milstein et al., *Nature,* 537:3053 (1983). The hybrid cell lines can be of any species, including human, rabbit and mouse.

In some embodiments, a cell line used in the methods of the invention is an antibody-producing cell line. Antibody-producing cell lines may be selected and cultured using techniques well known to the skilled artisan. See, e.g., *Current Protocols in Immunology*, Coligan et al., Eds., Green Publishing Associates and Wiley-Interscience, John Wiley and Sons, New York (1991) which is herein incorporated by reference in its entirety, including supplements.

In general, any cell suitable for recombinant protein expression in cell culture can be used in the methods of the invention.

In some embodiments, the cells used in the methods of the present invention may include a heterologous nucleic acid molecule which encodes a desired recombinant protein, e.g., a therapeutic protein or antibody which is desired to be produced using the methods of the invention. In a particular embodiment, the methods of the present invention are useful for producing high titers of a desired recombinant protein, e.g., a therapeutic protein or antibody, in the presence of reduced levels of one or more contaminants.

The term "cell culture," refers to cells grown in suspension, roller bottles, flasks and the like. Large scale approaches, such as bioreactors, including adherent cells growing attached to microcarriers in stirred fermentors, are also encompassed by the term "cell culture." Moreover, it is possible to not only to culture contact-dependent cells, but also to use the suspension culture techniques in the methods of the claimed invention. Exemplary microcarriers include, for example, dextran, collagen, plastic, gelatin and cellulose and others as described in Butler, Spier & Griffiths, *Animal cell Biotechnology* 3:283-303 (1988). Porous carriers, such as, for example, Cytoline® or Cytopore®, as well as dextran-based carriers, such as DEAE-dextran (Cytodex 1®), quaternary amine-coated dextran (Cytodex 2®) or gelatin-based carriers, such as gelatin-coated dextran (Cytodex 3®) may also be used. Cell culture procedures for both large and small-scale production of proteins are encompassed by the present invention. Procedures including, but not limited to, a fluidized bed bioreactor, hollow fiber bioreactor, roller bottle culture, or stirred tank bioreactor system may be used, with or without microcarriers, and operated alternatively in a batch, fed-batch, or perfusion mode.

The terms "cell culture medium," and "culture medium" refer to a nutrient solution used for growing animal cells, e.g., mammalian cells. Such a nutrient solution generally includes various factors necessary for cell attachment, growth, and maintenance of the cellular environment. For example, a typical nutrient solution may include a basal media formulation, various supplements depending on the cell type and, occasionally, antibiotics. In some embodiments, a nutrient solution may include at least one component from one or more of the following categories: 1) an energy source, usually in the form of a carbohydrate such as glucose; 2) all essential amino acids, and usually the basic set of twenty amino acids plus cystine; 3) vitamins and/or other organic compounds required at low concentrations; 4) free fatty acids; and 5) trace elements, where trace elements are defined as inorganic compounds or naturally occurring elements that are typically required at very low concentrations, usually in the micromolar range. The nutrient solution may optionally be supplemented with one or more components from any of the following categories: 1) hormones and other growth factors as, for example, insulin, transferrin, and epidermal growth factor; 2) salts and buffers as, for example, calcium, magnesium, and phosphate; 3) nucleosides and bases such as, for example, adenosine and thymidine, hypoxanthine; and 4) protein and tissue hydrolysates. In general, any suitable cell culture medium may be used. The medium may be comprised of serum, e.g. fetal bovine serum, calf serum or the like. Alternatively, the medium may be serum free, animal free, or protein free.

The terms "operably linked" and "operatively linked," as used interchangeably herein, refer to the positioning of two or more nucleotide sequences or sequence elements in a manner which permits them to function in their intended manner. In some embodiments, a nucleic acid molecule according to the invention includes one or more DNA elements capable of opening chromatin and/or maintaining chromatin in an open state operably linked to a nucleotide sequence encoding a recombinant protein. In other embodiments, a nucleic acid molecule includes one or more DNA elements capable of opening chromatin and/or maintaining chromatin in an open state operably linked to a nucleotide sequence encoding an apoptotic protein or a functional fragment thereof. In still other embodiments, a nucleic acid molecule may additionally include one or more nucleotide sequences chosen from: (a) a nucleotide sequence capable of increasing translation; (b) a nucleotide sequence capable of increasing secretion of the recombinant protein outside a cell; and (c) a nucleotide sequence capable of increasing the mRNA stability, where such nucleotide sequences are operatively linked to a nucleotide sequence encoding a recombinant protein. Generally, but not necessarily, the nucleotide sequences that are operably linked are contiguous and, where necessary, in reading frame. However, although an operably linked DNA element capable of opening chromatin and/or maintaining chromatin in an open state is generally located upstream of a nucleotide sequence encoding a recombinant protein or a nucleotide sequence encoding an apoptotic protein or functional fragment thereof, it is not necessarily contiguous with it. Operable linking of various nucleotide sequences is accomplished by recombinant methods well known in the art, e.g. using PCR methodology, by ligation at suitable restrictions sites or by annealing. Synthetic oligonucleotide linkers or adaptors can be used in accord with conventional practice if suitable restriction sites are not present.

The term "expression" as used herein refers to transcription and/or translation of a nucleotide sequence within a host cell. The level of expression of a desired product in a host cell may be determined on the basis of either the amount of corresponding mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by PCR. Proteins encoded by a selected sequence can be quantitated by various methods including, but not limited to, e.g., ELISA, Western blotting, radioimmunoassays, immunoprecipitation, assaying for the biological activity of the protein, or by immunostaining of the protein followed by FACS analysis.

The term "recombinant protein" or "recombinant polypeptide" produced by the methods of the invention generally refers to a peptide or protein, typically more than about ten amino acids in length produced by cells in culture using methods of the invention. A polypeptide produced by the methods of the invention is typically exogenous, i.e., heterologous or foreign, to the cells producing the polypeptide. Exemplary polypeptides produced by cells in culture using methods of the present invention include therapeutic proteins and antibodies and antigen binding fragments thereof. Also encompassed by the present invention are fusion proteins.

The term "immunoglobulin" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains). Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc and/or Fv fragments.

The term "antigen-binding fragment" refers to a polypeptide portion of an immunoglobulin or antibody that binds antigen or competes with intact antibody (i.e., with the intact antibody from which they were derived) for antigen binding (i.e., specific binding). Binding fragments can be produced by recombinant DNA techniques, or by enzymatic or chemical cleavage of intact immunoglobulins. Binding fragments include Fab, Fab', $F(ab')_2$, Fabc, Fv, single chains, and single-chain antibodies.

The terms "polynucleotide" and "nucleic acid molecule," used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. A nucleic acid molecule can take many different forms, e.g., a gene or gene fragment, one or more exons, one or more introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. As used herein, "DNA" or "nucleotide sequence" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. In a particular embodiment, a nucleic acid molecule comprises a nucleotide sequence encoding a recombinant protein such as, for example, a therapeutic protein or an antibody. In another embodiment, a nucleic acid molecule comprises a nucleotide sequence encoding an anti-apoptotic protein or a functional fragment thereof.

The term "anti-apoptotic protein," as used herein, refers to any protein or functional fragment thereof, which is encoded by an anti-apoptotic gene and/or has the ability to reduce, prevent or reverse one or more cellular responses associated with apoptosis. Apoptosis is known as an active cellular suicide program activated as a result of either extrinsic or intrinsic signals, such as serum deprivation, nutrient limitation, oxygen limitation and mechanical stress. Apoptosis is characterized by plasma membrane blebbing, cell volume loss, nuclear condensation, and endonuleolytic degradation of DNA at nucleosomal intervals. Accordingly, in some embodiments, an anti-apoptotic protein or functional fragment thereof is capable of reducing, preventing or reversing one or more of plasma membrane blebbing, cell volume loss, nuclear condensation, and endonuleolytic degradation of DNA at nucleosomal intervals in a cell. In some embodiments, an anti-apoptotic protein or functional fragment thereof enhances survival of a cell in which it is expressed. In some embodiments, an anti-apoptotic protein or functional fragment thereof is expressed in a host cell by introducing a nucleic acid molecule comprising a nucleotide sequence encoding the anti-apoptotic protein or functional fragment thereof operably linked to a DNA element capable of opening chromatin and/or maintaining chromatin in an open state. Exemplary nucleotide sequences include, but are not limited to, nucleotide sequences encoding for bcl-2 (Genbank Accession No. M14745); bcl-$x_L$; bcl-6; (Genbank Accession No. U001151); survivin; xiap (Genbank Accession No. NM_001167); hiap1; hiap2; aven (Genbank Accession No. NM_020371, SEQ ID NOs:5 and 6); E1B-19K (SEQ ID NO:7); P21; myrPHK; HSV-1 γ1 34.5; and beclin (Genbank Accession No. NM_003766), or a functional homolog or fragment thereof. In some embodiments, host cells are contacted with an isolated anti-apoptotic protein or functional homolog or fragment thereof. The functional anti-apoptotic activity of an anti-apoptotic protein, homolog or fragment thereof can be readily determined using one or more assays known in the art and those described herein. Exemplary assays include TUNEL assay, Annexin V assay, caspase assays, acridine orange/ethidium bromide staining or propidium iodide/acridine orange staining using fluorescence microscopy or flow cytometry analysis (see, e.g., *Current Protocols in Cytometry*, John Wiley & Sons, Inc.).

The term "a DNA element capable of opening chromatin and/or maintaining chromatin in an open state" refers to any DNA sequence or element which has the ability to make chromatin more accessible to transcription factors and facilitate reproducible expression of an operably-linked gene, where such a DNA sequence or element is not derived from a locus control region. Open chromatin or chromatin in an open state refers to chromatin in a de-condensed state and is also referred to as euchromatin. Condensed chromatin is also referred to as heterochromatin. Chromatin in a closed (condensed) state is transcriptionally silent. Whereas, chromatin in an open (de-condensed) state is transcriptionally competent. The establishment of an open chromatin structure is characterized by DNase I sensitivity, DNA hypomethylation and histone hyperacetylation. Standard methods for identifying open chromatin are well known to those skilled in the art and are described in Wu, 1989, *Meth. Enzymol.*, 170, 269-289; Crane-Robinson et al., 1997, *Methods*, 12, 48-56; Rein et al., 1998, *N. A. R*, 26, 2255-2264.

A "locus control region" (LCR) refers to a genetic element which is obtained from a tissue-specific locus of a eukaryotic host cell and which, when linked to a gene of interest and integrated into a chromosome of a host cell, confers tissue-specific, integration site-independent, copy number-dependent expression on the gene of interest.

Reproducible expression means that the DNA element when operably-linked to a gene of interest gives substantially the same level of expression of the operably-linked gene over an extended period of time irrespective of its chromatin environment and irrespective of the cell type. In some embodiments, substantially the same level of expression means a level of expression which has a standard deviation from an average value of less than 48%, or less than 40%, or less than 25% on a per-gene-copy basis. Alternatively, substantially the same level of expression means that the level of expression varies by less than 10 fold, less than 5 fold, or less than 3 fold on a per gene copy basis. In some embodiments, a DNA element capable of opening chromatin and/or maintaining chromatin in an open state increases the expression of an operably-linked gene by at least 2 fold, or at least 3 fold, or at least 4 fold, or at least 5 fold, or at least 10 fold, or at least 20 fold, or at least 30 fold, or at least 40 fold, or at least 50 fold, or at least 60 fold, or at least 70 fold, or at least 80 fold, or at least 90 fold, or at least 95 fold, or at least 100 fold, or at least 150 fold, or at least 200 fold, or more, relative to the expression without such an operably-linked DNA element. In some embodiments, a DNA element capable of opening chromatin and/or maintaining chromatin in an open state obtains a reproducible expression of an operably-linked gene over an extended period of time. For example, in some embodiments, an operably-linked gene is expressed at substantially the same level over a period of at least 5 days, 10 days, or at least 15 days, or at least 20 days, or at least 30 days, or at least 40 days, or at least 45 days, or at least 60 days, or at least 70 days, or at least 80 days, at least 90 days or more, relative to the expression level when the gene is not operably-linked to a DNA element capable of opening chromatin and/or maintaining chromatin in an open state. In other embodiments, an operably-linked gene is expressed at higher levels over an extended period of time relative to the levels when the gene is not operably-linked to a DNA element capable of opening chromatin and/or maintaining chromatin in an open state. Exemplary DNA elements capable of opening chromatin and/or maintaining chromatin in an open state include, but are not limited to, extended methylation-free CpG islands derived from the promoter regions of ubiquitously expressed genes (UCOEs), matrix and/or scaffolding attachment regions (MARs) and stabilizing and antirepressor regions (STARs). One skilled in the art can readily identify such DNA elements using well known assays in the art and those described herein.

In some embodiments, a DNA element capable of opening chromatin and/or maintaining chromatin in an open state is a naturally occurring DNA element. By naturally occurring DNA element, it is meant that the DNA element occurs in nature, e.g., it is isolated from the promoter region of a ubiquitously expressed gene, and its sequence is not altered from the naturally occurring sequence.

In other embodiments, a DNA element capable of opening chromatin and/or maintaining chromatin in an open state is an artificially synthesized DNA element. By artificially synthesized, it is meant that the DNA element does not occur in nature, e.g., a DNA element isolated from the promoter region of a ubiquitously expressed gene which is combined with a second DNA element isolated from the promoter region of another ubiquitously expressed gene, thereby resulting in an artificial construct, as the two elements do not normally occur together in nature. Alternatively, a DNA element may be modified in sequence using various techniques well known in the art from its naturally occurring sequence, thereby resulting in a DNA element that does not normally occur in nature.

In yet another embodiment, a DNA element capable of opening chromatin and/or maintaining chromatin in an open state is a combination of naturally occurring and artificially synthesized DNA elements.

The term "methylation-free CpG island" refers to CpG-islands have an average GC content of approximately 60%, compared with a 40% average in bulk DNA. One skilled in the art can easily identify CpG-islands using standard techniques such as restriction enzymes specific for C and G sequences, which are well known in the art. Exemplary methods for the identification of CpG islands can be found in, e.g., Gardiner-Garden et al., *J. Mol. Biol.* 1987, 196:261-82, incorporated by reference herein, and using computer programs such as CpG-plot which are readily available to one of ordinary skill in the art for analyzing and identifying CpG islands.

The term "an extended methylation-free CpG island," as used herein, refers to a methylation-free CpG island which is at least 300 bp, or at least 500 bp, or at least 1000 bp, or at least 1500 bp, or at least 2000 bp, or at least 2500 bp, or at least 3000 bp in length and is derived from the promoter region of a ubiquitously expressed gene. Such islands are well known in the art and are described in detail in U.S. Pat. Nos. 6,964,951; 6,689,606; 6,881,556; and 6,949,361 and PCT Application Publication No. WO 2004/067701, each of which is incorporated by reference herein in their entirety.

In some embodiments, an extended methylation-free CpG island includes one or more transcription factor binding sites. In other embodiments, an extended methylation-free CpG island includes a promoter and/or enhancer sequence. In yet other embodiments, an extended methylation-free CpG island includes a dual or bi-directional promoter. Although an extended methylation-free CpG island may include a promoter, as used herein, such islands are typically used in conjunction with one or more heterologous promoters which are not typically associated with the island, e.g., human or guinea pig CMV promoter. In some embodiments, a heterologous promoter replaces the endogenous promoter found within the CpG island.

Extended methylation-free CpG islands can be defined, e.g., by identifying the borders of such islands. For example, the borders of the extended methylation-free CpG islands can be defined through the use of PCR in combination with restriction endonuclease enzymes whose ability to digest (cut) DNA at their recognition sequence is sensitive to the methylation status of any CpG residues that are present. One such enzyme is HpaII, which recognizes and digests at the site CCGG, which is commonly found within CpG islands, but only if the central CG residues are not methylated. Therefore, PCR conducted with HpaII-digested DNA and over a region harboring HpaII sites, does not give an amplification product due to HpaII digestion if the DNA is unmethylated. The PCR will only give an amplified product if the DNA is methylated. Therefore, beyond the methylation-free region, HpaII will not digest the DNA a PCR amplified product will be observed thereby defining the boundaries of the "extended methylation-free CpG island."

Exemplary extended methylation-free CpG islands include, but are not limited to, those derived from the promoter regions of the human RNPA2 gene (SEQ ID NOs:2, 3 and 4), RPS3 gene (Accession No. NM012052; SEQ ID NO:1), RPL4 gene (Accession No. NT_039474), RPL5 gene (NT_039308), RPL10a gene (Accession No. NT_039649), RPL13a gene (Accession No. NT_039420), RPL19 gene (Accession No. NT_039521), RPL24 gene (Accession No. NT_096987), RPL27a gene (Accession No. NT_039433), Terf2ip gene (Accession No. AB041557), human glyceryldehyde-3 phosphate dehydrogenase gene (Accession No. M32599), tubulin alpha-1 chain gene (Accession No. M13445), and RPS11 gene (Accession No. AK011207). Additional examples of ubiquitously expressed or housekeeping genes can be found in, e.g., *Trends in Genetics* 19, 362-365 (2003), incorporated by reference herein.

The term "matrix attachment region," or "scaffold attachment region," or "scaffold/matrix attachment region," or "MAR" or "S/MAR," as used interchangeably herein, refers to a DNA element which is capable of binding isolated nuclear scaffolds or nuclear matrices in vitro with high affinity. (See, e.g., Hart and Laemmli (1988) *Curr. Opin. Genet. Dev.*, 8:519-525). It has been reported that MAR DNA elements can increase expression of a heterologous gene in cell culture. (See, e.g., Kalos and Fournier (1995) *Mol. Cell Biol.* 15:198-207; Phi-Van et al. (1990) *Mol. Cell Biol.* 10:2302-2307; Klehr et al. (1991) *Biochemistry* 30:1264-1270; and Poljak et al. (1994) *Nuc. Acid Res.* 22:4386-4394). Exemplary MAR DNA elements can be found in, for example, U.S. Pat. No. 7,129,062, incorporated by reference herein in its entirety. In a particular embodiment, a MAR element used in the methods of the invention is a chicken lysozyme MAR element, as set forth in U.S. Pat. No. 7,129,062, and functional fragments thereof. One skilled in the art can readily identify MAR elements based on the well known assays in the art coupled with those described herein, e.g., those described in Mesner et al. (2003) *Proc. Natl. Acad. Sci.*, 3281-3286 and Weber et al., *Mol Cell Biol.* (2003) December; 23(24): 8953-8959. In another embodiment, a MAR DNA element used in the methods of the invention is a human β-globin MAR element. Exemplary MAR DNA elements which may be used in the methods of the invention are set forth in SEQ ID NOs:11-14.

The term "stabilizing and antirepressor region" or "STAR" refers to a DNA element which has the ability to block heterochromatin-mediated transgene expression. STAR DNA elements can be readily identified using known techniques for assaying for gene transcription modulating properties of DNA elements, e.g., those described in WO03/004704, WO 2004/056986 and EP01202581.3, incorporated by reference herein in their entirety. Non-limiting examples of STAR sequences which may be used in the methods of invention include sequence set forth in SEQ. ID. NOs. 1-66 in US Patent Publication No. 20060141577.

The term "a nucleotide sequence capable of increasing translation" refers to a nucleotide sequence which is capable of increasing the synthesis of a polypeptide from an mRNA. An increase in synthesis of the polypeptide can either be an increase in the overall amount of the polypeptide produced or an increase in the rate of synthesis of the polypeptide. In one embodiment, a nucleotide sequence capable of increasing translation is operably linked to a nucleotide sequence encoding a recombinant protein. The ability of the nucleotide sequence capable of increasing translation and be measured by assaying for an increase in the amount of the recombinant protein produced in the presence of the nucleotide sequence capable of increasing translation or by the rate of synthesis of the recombinant protein over time.

The term "a nucleotide sequence capable of increasing secretion" refers to a nucleotide sequence, which when operably linked to a nucleotide sequence encoding a protein, has the ability to promote secretion of the protein outside the cell. Typically, such a nucleotide sequence comprises an appropriate native or heterologous signal peptide (leader sequence). The choice of signal peptide or leader depends on the type of host cells in which the recombinant protein is to be produced, and a heterologous signal peptide can replace the native signal sequence. Exemplary sequences which may be used in the methods of the invention include, for example, a signal peptide derived from a luciferase gene from *Gaussia princeps* (Genbank Accession No. AY015993). Nucleotide sequences which are capable of increasing secretion, also referred to as signal peptide sequences, can be identified using software programs well known in the art, such as, for example, SignalP Server (http://www.cbs.dtu.dk/services/SignalP).

The term "a nucleotide sequence capable of increasing mRNA stability," as used herein, refers to a nucleotide sequence, which when operably linked to a nucleotide sequence encoding a recombinant protein, increases the half-life of the mRNA which is translated into the recombinant protein. Typically, such nucleotide sequences are derived from the 3' or 5' untranslated regions (or UTRs) of genes.

II. EXEMPLARY CELLS

Without wishing to be bound by theory, it is contemplated that any cell line which is capable of producing a recombinant protein may be used in the methods of the invention. In a particular embodiment, cells used in the methods of the invention are transfected with a nucleic acid molecule comprising a nucleotide sequence encoding a recombinant polypeptide, e.g., a therapeutic protein or an antibody. In a particular embodiment, the cells used in the methods of the invention are eukaryotic cells, e.g., mammalian cells. Examples of mammalian cells include, but are not limited to, for example, monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells/-DHFR (CHO, Urlaub and Chasin, *Proc. Natl. Acad. Sci. USA*, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; NSO mouse myeloma cells (ECACC; SIGMA), and a human hepatoma line (Hep G2). Additional examples of useful cell lines include, but are not limited to, HT1080 cells (ATCC CCL 121), MCF-7 breast cancer cells (ATCC BTH 22), K-562 leukemia cells (ATCC CCL 243), KB carcinoma cells (ATCC CCL 17), 2780AD ovarian carcinoma cells (see Van der Blick, A. M. et al., *Cancer Res.* 48:5927-5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. These and other cells and cell lines are available commercially, for example from the American Type Culture Collection (Virginia, USA). Many other cell lines are known in the art and will be familiar to the ordinarily skilled artisan; such cell lines therefore can be used equally well in the methods of the present invention. In a particular embodiment, cells used in the methods of the invention are CHO cells or NSO cells.

Hybridomas and antibody-producing cells may also be used in the methods of the invention.

III. EXEMPLARY NUCLEOTIDE SEQUENCES AND VECTORS

In some embodiments, a first nucleic acid comprising a nucleotide sequence encoding a recombinant protein of interest is introduced into a host cell, along with a second nucleic acid molecule comprising a nucleotide sequence encoding an anti-apoptotic protein or functional fragment thereof. For example, a first nucleic acid molecule comprising a nucleotide sequence encoding a desired recombinant protein of interest is cloned into a suitable expression vector, which includes the nucleotide sequence encoding the recombinant protein operably linked to a DNA element capable of opening chromatin and/or maintaining chromatin in an open state. Additionally, a second nucleic acid molecule comprising a nucleotide sequence encoding an anti-apoptotic protein or functional fragment thereof is cloned into the same expression vector as the recombinant protein or a different expression vector, where the nucleotide sequence encoding the anti-apoptotic protein or functional fragment thereof is also operably linked to a DNA element capable of opening chromatin and/or maintaining chromatin in an open state.

Any suitable vector may be used according to the invention. Nucleotide sequences can be stably integrated into the host cell genome using, for example, retroviral (Miller, 1992, *Curr. Top. Microbiol. Immunol.* 158:1; Miller et al., 1993, *Meth. Enzymol.* 217: 581) or adeno-associated viral (MV) vectors (Muzyczka, 1992, *Curr. Top. Microbiol. Immunol.*, 158: 97; Flotte and Carter, 1995, *Gene Ther.* 2: 357). Alternatively, nucleotide sequences encoding proteins can be incorporated within self-replicating episomal vectors comprising viral origins of replication such as those from EBV (Yates et al., 1985, *Nature* 313: 812), human papovavirus BK (De Benedetti and Rhoads, 1991, *Nucl. Acids Res.*, 19: 1925; Cooper and Miron, 1993, *Hum. Gene Ther.* 4: 557; and BPV-1 (Piirsoo et al., 1996, *EMBO J.* 15:1).

Vectors and methods for genetically engineering cells and/or cell lines to express a protein of interest are well known to those skilled in the art; for example, various techniques are illustrated in Current Protocols in Molecular Biology, Ausubel et al., eds. (Wiley & Sons, New York, 1988, and quarterly updates); Sambrook et al., Molecular Cloning: A Laboratory Manual (Cold Spring Laboratory Press, 1989) and Kaufman, R. J., Large Scale Mammalian Cell Culture (1990, pp. 15-69).

Additional regulatory sequences may also be included in the expression vectors described herein. These may be derived from mammalian, microbial, viral, and/or insect genes. Examples of regulatory sequences include transcriptional promoters, operators, and enhancers, ribosome binding sites (see e.g. Kozak (1991), *J. Biol. Chem.* 266:19867-70), sequences that can control transcriptional and translational termination, and polyadenylation signals (see e.g. McLauchlan et al. (1988), *Nucleic Acids Res.* 16:5323-33). In some embodiments, expression vectors used in the methods of the invention include a human or a guinea pig CMV promoter.

Some commonly used promoter and enhancer sequences are derived from viral genomes, for example polyoma virus, adenovirus 2, simian virus 40 (SV40), and human cytomegalovirus. For example, the human CMV promoter/enhancer of immediate early gene 1 may be used (see, e.g., Patterson et al.

(1994), *Applied Microbiol Biotechnol.* 40:691-98). DNA sequences derived from the SV40 viral genome, for example, SV40 origin, early and late promoter, enhancer, splice, and polyadenylation sites can be used to provide other genetic elements for expression of a polypeptide in a eukaryotic host cell. Viral early and late promoters are particularly useful because both are easily obtained from a viral genome as a fragment, which can optionally also contain a viral origin of replication (Fiers et al. (1978), *Nature* 273:113; Kaufman (1990), *Meth. in Enzymol.* 185:487-511). Smaller or larger SV40 fragments can also be used.

In some embodiments, a nucleotide sequence encoding a recombinant protein is operably-linked to one or more nucleotide sequences chosen from: (a) a nucleotide sequence capable of increasing translation; (b) a nucleotide sequence capable of increasing secretion; and (c) a nucleotide sequence capable of increasing mRNA stability.

Additional control sequences shown to improve expression of heterologous genes from mammalian expression vectors include such elements as the expression augmenting sequence element (EASE) derived from CHO cells (Morris et al., *Animal Cell Technology*, pp. 529-534 (1997); U.S. Pat. No. 6,312,951 B I; U.S. Pat. No. 6,027,915; U.S. Pat. No. 6,309,841 B 1) and the tripartite leader (TPL) and VA gene RNAs from Adenovirus 2 (Gingeras et al. (1982), *J. Biol. Chem.* 257:13475-13491) and Internal ribosome entry site (IRES) sequences that allow mRNAs to be translated efficiently.

A gene encoding a selectable marker is often used to facilitate the identification of recombinant cells. Selection of transformants can be performed using methods such as, for example, the dihydrofolate reductase (DHTR) selection scheme or resistance to cytotoxic drugs (see, e.g., Kaufman et al. (1990), *Meth. in Enzymology* 185:487-511). A suitable cell line for DHFR selection can be, for example, CHO line DX-B 11, which is deficient in DHFR (see, e.g., Urlaub and Chasin (1980), *Proc. Natl Acad. Sci. USA* 77:4216-4220). Other examples of selectable markers include those conferring resistance to antibiotics, such as G418 and hygromycin B.

In certain embodiments of the invention, a gene encoding for a selectable marker is not necessary due to the use of a DNA element capable of opening chromatin and/or maintaining chromatin in an open state, as pools of cells can be used instead of having to select a particular clone which expresses a recombinant protein.

In some embodiments, an exogenous nucleic acid which is used for producing a protein by the methods according to the invention is isolated from a cDNA library or a genomic library. For example, in order to isolate a nucleic acid encoding a protein of interest, a cDNA library may be screened with probes designed to identify the gene or a cDNA clone encoding the protein. For cDNA expression libraries, suitable probes include monoclonal or polyclonal antibodies that recognize and specifically bind to the protein of interest; oligonucleotides of about 20-80 bases in length that encode known or suspected portions of the protein from the same or different species; and/or complementary or homologous cDNAs or fragments thereof for the same or a similar gene. Appropriate probes for screening genomic DNA libraries include, but are not limited to, oligonucleotides, cDNAs, or fragments thereof that encode the same or a similar gene, and/or homologous genomic DNAs or fragments thereof. Screening the cDNA or genomic library with the selected probe may be conducted using standard procedures as described in chapters 10-12 of Sambrook et al., Molecular Cloning: A Laboratory Manual (New York: Cold Spring Harbor Laboratory Press, 1989).

In various embodiments described herein, particular sequences described herein as well as homologs and fragments of such sequences can be used in the methods of the invention, so long as they have the desired activity. For example, in some embodiments, sequences that are at least 70% identical, or at least 80% identical, or at least 90% identical, or at least 95% or more identical, to particular sequences encompassed by the present invention are useful in the methods of the invention.

IV. EXEMPLARY ANTI-APOPTOTIC GENES AND PROTEINS

There are two general ways by which cells die. An easily recognized pathway is necrosis, a process of cell death usually resulting from severe and sudden injury. In necrosis, changes in cellular homeostasis occur with loss of membrane integrity. Deregulation of osmotic pressure results and cells swell and finally rupture. The cellular contents are then spilled into the surrounding tissue space and, usually, an inflammation response ensues. This may be contrasted with a second form of cell death, apoptosis.

Apoptosis or the cell "suicide" pathway or "programmed cell death" often occurs rapidly and is a process in the cell actively participates in its own demise. Apoptosis is defined predominantly by morphological criteria. The characteristic features of apoptosis include cell shrinkage, chromatin condensation, and DNA fragmentation into oligonucleosomal ladder size units. Finally, fragments of the dying cell form sealed vesicles called apoptotic bodies which are rapidly removed by neighboring cells (Wylie, et al., 1980, *Int. Rev. Cytol.*, 68:251).

A number of genes in eukaryotic cells have been identified which inhibit the onset or reduce the effects of apoptosis. Some of these genes inhibit caspase dependent apoptotic pathways in cell. Cells grown to high density in scale up bioreactors show an increased susceptibility to apoptosis perhaps due in part to the serum free conditions for growth (Zanghi et al. 1999, *Biotechnol. Bioeng.* 64:108). Other conditions possibly contributing to apoptosis include growth factor withdrawal, ionizing radiation and oxidative stress. Transfecting cells with apoptotic genes has been described (Al-Rubeai et al. 1998, *Current Opinion Biotech* 9(2):152). Transfecting cells with anti-apoptotic genes may be useful in prolonging the life and productivity of transfected cells grown under biologically demanding conditions, thereby creating a healthier more robust cell.

Thus certain embodiments of the invention provide for cells engineered to express levels of anti-apoptotic genes sufficient to reduce the onset or effects of apoptosis in cell culture, e.g. culture vessels ranging in size from T25 flasks, or smaller, to scale up bioreactors, or larger. The cells may be transfected with one or more copies of an anti-apoptotic gene or a functional fragment thereof. A functional fragment of an anti-apoptotic gene may comprise less than the full length sequence of the cloned gene, but still maintain the ability of reducing the onset or effects of apoptosis in cultured cells. Where multiple copies of anti-apoptotic genes are used the genes may all be the same gene or may be comprised of a mixture of 2 or more different genes. Examples of anti-apoptotic genes suitable for use in the present invention include bcl family members such as bcl-2 (Genbank Accession No. M14745); bcl-$x_L$; bcl-6; aven (SEQ ID NOs:5 and 6), mcl-1: survivin (U.S. Pat. No. 6,077,709); xiap (Genbank Accession No. NM_001167); hiap1, hiap2 (U.S. Pat. No. 5,919,912); E1B-19K (SEQ ID NO:7) and P21; myrPHK; HSV-1 γ1 34.5 (U.S. Pat. No. 6,172,047); and beclin (U.S. Pat. No. 6,432, 914); p35; ced9; Crm A; BHFR (Al-Rubeai et al. 1998, Current Opinion Biotech 9(2):152).

In some embodiments, cells are transfected with a nucleotide molecule comprising a nucleotide sequence encoding an anti-apoptotic gene or functional fragment thereof operably linked to a DNA element capable of opening chromatin and/or maintaining chromatin in an open state.

In some embodiments, use of a DNA element capable of opening chromatin and/or maintaining chromatin in an open state results in a greater percentage of cells (e.g., at least 40%, at least 50%, at least 60%, at least 70%, at least 80%, at least 90%, at least 95%, or more) expressing the operably-linked anti-apoptotic gene over an extended period of time relative to cells where the gene is not operably-linked to a DNA element capable of opening chromatin and/or maintaining chromatin in an open state, thereby eliminating the need for a selection step, and/or an amplification step.

In some embodiments, the methods of the invention eliminate the need for a gene amplification step.

In some embodiments, cells expressing a desired recombinant protein in conjunction with an anti-apoptotic protein or functional fragment thereof result in a lower level of one or more contaminants relative to cells which express the recombinant protein alone, thereby improving the overall quality as well as quantity of the recombinant protein produced as well as reducing both the time as well as the resources associated with the harvesting of the recombinant protein.

V. EXEMPLARY RECOMBINANT PROTEINS

The methods of the invention can be used to produce any desired recombinant protein or fragment thereof. In some embodiments, a recombinant protein produced using the methods described herein is a therapeutic protein. In other embodiments, the recombinant protein is an antibody or functional fragment thereof. Antibodies which may be produced using the methods of the invention include, for example, polyclonal, monoclonal, monospecific, polyspecific, fully human, humanized, single-chain, chimeric, hybrid, mutated, and CDR-grafted antibodies, and antigen-binding fragments thereof, such as, for example, Fab, F(ab')$_2$, Fv, and scfv. The antibodies can be specific for any desirable antigen comprising a suitable epitope. Desirable antigens may include for example, a marker found in or associated with a mammalian cell, a marker associated with a tumor or a marker associated with a disease or condition. Examples of tumor markers include tumor antigen CA 125, tumor antigen gp72 LCG (which is a gene product that is expressed in association with lung cancer), HER-2, a tumor-associated glycoprotein, and tumor antigen MUC 1. Other markers for cancer include hTERT (Ferber et al. 2003, *Oncogene* 22:3813), Ki-67 (Kruse et al. 2002, *Am. J. Surg. Pathol.,* 26:1501), cyclin E (Yasmeen et al. 2003, *Expert Rev. Mol. Diagn.* 3(5):617) and histone H3 (Rakowicz-Szulczynska, et al. 1996, *Cancer Biother. Radiopharm.* 11:77).

In some embodiments, methods of the invention are used for producing high titers of antibodies or antigen-binding fragments thereof. An antibody may be specific to a cell surface protein such as a growth factor or hormone receptor.

Antibodies within the scope of the present invention include, but are not limited to: anti-HER2 antibodies including Trastuzumab (HERCEPTIN®) (Carter et al., *Proc. Natl. Acad. Sci. USA,* 89:4285-4289 (1992), U.S. Pat. No. 5,725,856); anti-CD20 antibodies such as chimeric anti-CD20 "C2B8" as in U.S. Pat. No. 5,736,137 (RITUXAN®), a chimeric or humanized variant of the 2H7 antibody as in U.S. Pat. No. 5,721,108, B1, or Tositumomab (BEXXAR®); anti-IL-8 (St John et al., *Chest,* 103:932 (1993), and International Publication No. WO 95/23865); anti-VEGF antibodies including humanized and/or affinity matured anti-VEGF antibodies such as the humanized anti-VEGF antibody huA4.6.1 AVASTIN®. (Kim et al., *Growth Factors,* 7:53-64 (1992), International Publication No. WO 96/30046, and WO 98/45331, published Oct. 15, 1998); anti-PSCA antibodies (WO01/40309); anti-CD40 antibodies, including S2C6 and humanized variants thereof (WO00/75348); anti-CD11a (U.S. Pat. No. 5,622,700, WO 98/23761, Steppe et al., *Transplant Intl.* 4:3-7 (1991), and Hourmant et al., *Transplantation* 58:377-380 (1994)); anti-IgE (Presta et al., *J. Immunol.* 151: 2623-2632 (1993), and International Publication No. WO 95/19181); anti-CD18 (U.S. Pat. No. 5,622,700, issued Apr. 22, 1997, or as in WO 97/26912, published Jul. 31, 1997); anti-IgE (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338); anti-Apo-2 receptor antibody (WO 98/51793 published Nov. 19, 1998); anti-TNF-α antibodies including cA2 (REMICADE®), CDP571 and MAK-195 (See, U.S. Pat. No. 5,672,347 issued Sep. 30, 1997, Lorenz et al. *J. Immunol.* 156(4):1646-1653 (1996), and Dhainaut et al. *Crit. Care Med.* 23(9):1461-1469 (1995)); anti-Tissue Factor (TF) (European Patent No. 0 420 937 B1 granted Nov. 9, 1994); anti-human $\alpha_4\beta_7$ integrin (WO 98/06248 published Feb. 19, 1998); anti-EGFR (chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-tac antibodies such as CHI-621 (SIMULECT®) and (ZENAPAX®) (See U.S. Pat. No. 5,693,762 issued Dec. 2, 1997); anti-CD4 antibodies such as the cM-7412 antibody (Choy et al. *Arthritis Rheum* 39(1):52-56 (1996)); anti-CD52 antibodies such as CAMPATH-1H (Riechmann et al. *Nature* 332: 323-337 (1988)); anti-Fc receptor antibodies such as the M22 antibody directed against FcγRI as in Graziano et al. *J. Immunol.* 155(10):4996-5002 (1995); anti-carcinoembryonic antigen (CEA) antibodies such as hMN-14 (Sharkey et al. *Cancer Res.* 55(23Suppl): 5935s-5945s (1995); antibodies directed against breast epithelial cells including huBrE-3, hu-Mc 3 and CHL6 (Ceriani et al. *Cancer Res.* 55(23): 5852s-5856s (1995); and Richman et al. *Cancer Res.* 55(23 Supp): 5916s-5920s (1995)); antibodies that bind to colon carcinoma cells such as C242 (Litton et al. *Eur J. Immunol.* 26(1):1-9 (1996)); anti-CD38 antibodies, e.g. AT 13/5 (Ellis et al. *J Immunol.* 155(2):925-937 (1995)); anti-CD33 antibodies such as Hu M195 (Jurcic et al. *Cancer Res* 55(23 Suppl):5908s-5910s (1995) and CMA-676 or CDP771; anti-CD22 antibodies such as LL2 or LymphoCide (Juweid et al. *Cancer Res* 55(23 Suppl):5899s-5907s (1995)); anti-EpCAM antibodies such as 17-1A (PANOREX®); anti-GpIIb/IIIa antibodies such as abciximab or c7E3 Fab (REOPRO®); anti-RSV antibodies such as MEDI-493 (SYNAGIS®); anti-CMV antibodies such as PROTOVIR®; anti-HIV antibodies such as PRO542; antihepatitis antibodies such as the anti-Hep B antibody OSTAVIR®; anti-CA 125 antibody OvaRex; anti-idiotypic GD3 epitope antibody BEC2; anti-αvβ3 antibody VITAXIN®; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1). The preferred target antigens for the antibody herein are: HER2 receptor, VEGF, IgE, CD20, CD11a, and CD40.

The recombinant protein may be a cellular protein such as a receptor (e.g., membrane bound or cytosolic) or a structural protein (e.g. a cytoskelatal protein). The recombinant protein may be cellular factor secreted by the cell or used internally in one or more signal transduction pathways. Non limiting examples include, but are not limited to, CD2, CD3, CD4, CD8, CD11a, CD14, CD18, CD20, CD22, CD23, CD25, CD33, CD40, CD44, CD52, CD80 (B7.1), CD86 (B7.2), CD147, IL-1, IL-2, IL-3, IL-7, IL-4, IL-5, IL-8, IL-10, IL-2 receptor, IL-4 receptor, IL-6 receptor, IL-13 receptor, IL-18 receptor subunits, PDGF, EGF receptor, VEGF receptor, hepatocyte growth factor, osteoprotegerin ligand, interferon gamma, B lymphocyte stimulator C5 complement TAG-72, integrin alpha 4 beta 7, the integrin VLA-4, B2 integrins, TRAIL receptors 1, 2, 3, and 4, RANK, RANK ligand, TNF, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2, and CTLA4 (which is a cytotoxic T lymphocyte-associated antigen).

The recombinant protein may also be derived from an infectious agent such as a virus, a bacteria, or fungus. For example, the protein may be derived from a viral coat or may be a viral enzyme or transcription factor. The protein may be derived from a bacterial membrane or cell wall, or may be derived from the bacterial cytosol. The protein may be a yeast enzyme, transcription factor, or structural protein. The yeast protein may be membrane bound, cytsolic, or secreted. Examples of infectious agents include, but are not limited to, respiratory syncitial virus, human immunodeficiency virus (HIV), hepatitis B virus (HBV), hepatitis C virus (HCV), *Streptococcus mutans*, and *Staphlycoccus aureus*, and *Candida albicans*.

The methods of the invention can also be used to produce recombinant fusion proteins comprising all or part of any of the above-mentioned proteins. For example, recombinant fusion proteins comprising one of the above-mentioned proteins plus a multimerization domain, such as a leucine zipper, a coiled coil, an Fc portion of an antibody, or a substantially similar protein, can be produced using the methods of the invention. See e.g. International Application No. WO 94/10308; Lovejoy et al. (1993), *Science* 259:1288-1293; Harbury et al. (1993), *Science* 262: 1401-05; Harbury et al. (1994), *Nature* 371:80-83; Hang.kansson et al. (1999), *Structure* 7:255-64.

Also encompassed by this invention are pharmaceutical compositions including one or more recombinant proteins produced by the methods described herein. In some embodiments, pharmaceutical compositions further include a pharmaceutically acceptable carrier. The term "pharmaceutically-acceptable carrier" as used herein means one or more compatible solid or liquid filler, diluents or encapsulating substances which are suitable for administration into a subject.

VI. METHODS OF INTRODUCING NUCLEOTIDE SEQUENCES AND VECTORS INTO CELLS

The methods of the invention are useful for the production of recombinant proteins in the presence of reduced levels of one or more contaminants, and in particular, for the production of therapeutic proteins and antibodies in the presence of reduced levels of one or more contaminants. Protocols for introducing nucleotide sequences and vectors into cells are well known in the art including various commercially available reagents, such as the cationic lipid reagents LIPOFECTAMINE™, LIPOFECTAMINE™-2000, or LIPOFECTAMINE™-PLUS (INVITROGEN), can be used to transfect cells (see, e.g., Feigner et al. (1987), *Proc. Natl. Acad. Sci. USA* 84:7413-7417). In addition, electroporation or bombardment with microprojectiles coated with nucleic acids can be used to transfect cells using procedures, such as those in Sambrook et al., *Molecular Cloning: A Laboratory Manual,* 2nd ed. Vol. 1-3 (Cold Spring Harbor Laboratory Press, 1989) and Fitzpatrick-McElligott ((1992), *Biotechnology* (NY) 10(9):1036-40). Genetic engineering techniques include, but are not limited to, transfection, transformation, and/or transduction of cells with expression vectors, targeted homologous recombination and gene activation (see e.g. U.S. Pat. No. 5,272,071 to Chappel), and transactivation by engineered transcription factors (see e.g. Segal et al. (1999), *Proc. Natl. Acad. Sci. USA* 96(6):2758-63).

In a particular embodiment, high efficiency controlled electroporation is used for introducing the various nucleic acid molecules into a host cell. Exemplary devices and methods for performing controlled electroporation can be found, for example, in U.S. Pat. Nos. 6,300,108; 6,562,604; 6,387,671; 6,403,348; 6,482,619; 7,053,063, each of which are incorporated by reference herein in their entirety.

Controlled electroporation is based upon the discovery that the onset and extent of electroporation in a biological cell can be correlated to changes in the electrical impedance (which as used herein means the ratio of current to voltage) of the biological cell or of a conductive medium that includes the biological cell. An increase in the current-to-voltage ratio across a biological cell occurs when the cell membrane becomes permeable due to pore formation. Likewise, a decrease in the current-to-voltage ratio through a flowing conductive fluid occurs when the fluid draws a biological cell into the region between the electrodes in a flow-through electric cell. Thus, by monitoring the impedance of the biological cell or of an electrolyte solution in which the cell is suspended, one can detect the point in time in which pore formation in the cell membrane occurs, as well as the relative degree of cell membrane permeability due to the pore formation. This information can then be used to establish that a given cell has in fact undergone electroporation, or to control the electroporation process by governing the selection of the voltage magnitude. Controlled electroporation may also be useful in the simultaneous electroporation of a plurality of cells, since it provides a direct indication of the actual occurrence of electroporation and an indication of the degree of electroporation averaged over the cells. The method is likewise useful in the electroporation of biological tissue (masses of biological cells with contiguous membranes) for the same reasons.

Controlled electroporation involves the use of an electroporation device in which a biological cell can be placed and which contains a barrier that directs the electric current flow and hence the ion flow through a flow path that passes through the biological cell while permitting substantially no electric current to bypass the biological cell. It involves the use of an apparatus containing two liquid-retaining chambers separated by a barrier that is substantially impermeable to an electric current. The barrier contains an opening that is smaller than the biological cell such that the biological cell once lodged in the opening will plug or close the opening. To achieve electroporation, the biological cell is secured over the opening by mechanical or chemical means, e.g., in a reversible manner so that the biological cell can later be removed without damage to the biological cell. Once the biological cell is secured over the opening, a voltage is imposed between the two chambers and across the biological cell residing in the opening. The passage of current between the chambers is thus restricted to a path passing through the opening and hence through the biological cell. By monitoring the current-voltage relation in the electric cell, the onset of electroporation is detected and the degree of pore formation is controlled, to both assure that electroporation is occurring and to prevent excessive pore formation and cell death. The user is thus afforded a highly precise knowledge and control of the condition of and the flux across the biological cell membrane. The device may thus comprise two electrodes. The polarity of each respective electrode may be alternated back and forth thus permitting penetration of a target nucleic acid through the cell membrane from at least two distinct points. For example, the points may be approximately 180° apart in a plane of the cell.

The electroporation device may comprise an internal support to hold a single biological cell, or a plurality of biological cells, and an internal barrier that restricts the electric current flow in the device to a flow path that passes through the biological cell. The electroporation device may comprise one or more chambers suitable for holding a buffer. Where a plurality of chambers is present each chamber may hold the same buffer, or a different buffer. When no voltage is applied, the structure can be used for diffusive transport alone, unassisted by voltage-induced pore formation. The configuration of the barrier, and the two chambers in embodiments that include two chambers, is not critical to the electroporation cell, and can vary widely while still serving its purpose. Since biological cells are microscopic in size, however, the apparatus may be the size of electronic chips, fabricated by microfabrication techniques such as those used in electronic chip manufacture. The chambers may be constructed as flow-through chambers to allow the passage of the liquids in continuous flow, intermittent flow, or flow at the direction of the user, and to allow changes in the concentrations, pressure, and other conditions as needed to achieve close control over the passage of species across the biological cell membrane. The apparatus may comprise layers or platelets with appropriate openings that form flow passages when the layers or platelets are bonded together.

Flow-through chambers offer the advantage of permitting the successive entry and removal of individual cells so that large numbers of cells can be treated in succession. Flow-through chambers also permit replenishment of solute-depleted solutions so that concentration gradients can be continuously maintained when desired. A further function that can be served by flow-through chambers is the increase and decrease of pressure, a function that is useful for various purposes as described below.

The support for the biological cell in this structure can be any structure that secures the biological cell in a fixed position and that allows the passage of electric current. The most convenient support is an opening in the barrier. Securing a biological cell over the opening serves to close, seal or plug the opening, thereby directing the passage of electric current, diffusive transport, or both, through the cell and eliminating or minimizing leakage around the cell. A mechanical means of achieving this is to impose a pressure differential across the opening in a direction that will press the cell against the opening. The diameter of the opening may be smaller than that of the cell, and the cell upon entering the apparatus will pass into one of the two chambers. By increasing the pressure in the chamber in which the cell resides, or lowering the pressure in the other chamber, the cell will be forced against the opening, closing it off. Once the procedure is completed, the cell is readily released from the opening by equalizing the pressures in the two chambers or by reversing the differential such that the higher pressure is in the chamber other than the chamber in which the cell was introduced. The flow of liquid in the chamber in which the cell was introduced will then remove the cell from the opening, exposing the opening for another cell.

An alternative method of sealing the opening with the cell is by the use of a coating on the barrier surface, or over the rim of the opening, of a substance that binds to the cell membrane. Since biological cell membranes are negatively charged, the coating may be a substance that bears a positive charge, such as polylysine, polyarginine, or polyhistidine. The biological cell can be directed to the opening by a pressure differential across the opening, and held in place by the coating. Once the procedure is completed, the cell can be released from the coating by momentarily increasing the flow rate of the liquid in the chamber on the cell side of the opening, or by imposing a reverse pressure differential across the opening to urge the cell away from the opening.

In another aspect, controlled electroporation is performed using an electroporation device such as, e.g., described in Wang et al., *Anal. Chem*, (2006) 78:5158-5164.

In one aspect, high efficiency controlled electroporation is performed using a device which includes one or more capillaries. The method of controlled electroporation comprises the steps of: 1) placing the one or more cells in an electroporation device comprising at least one elongate capillary having a lumen comprising a first end and a second end, where both the first end and the second end open into reservoirs and where the one or more cells can flow through the lumen of the at least one capillary and into the reservoirs; 2) contacting the one or more cells with a nucleic acid molecule comprising one or more DNA elements capable of opening chromatin and/or maintaining chromatin in an open state operably linked to a nucleotide sequence encoding the recombinant protein; 3) contacting the one or more cells with an electric current such that the current passes through the one or more cells; 4) monitoring the ratio between the current and voltage in the electroporation device; and 5) adjusting the magnitude of the local field strength to a field strength suitable to achieve electroporation of the one or more cells.

In some embodiments, the diameter of the lumen of a capillary is no greater than about 20% of the diameter of a cell in the lumen. In some embodiments, the diameter of the lumen of the capillary is no greater than about 20% of the diameter of a plurality of cells (e.g., the perimeter around a group of cells in the lumen).

In various controlled electroporation methods described herein, the optimal local field strength suitable for achieving the electroporation of a particular cell type can be readily determined using known methods in the art, e.g., by assaying for a change (e.g., an increase) in cell diameter over time when the cell is exposed to varying field strengths. In some embodiments, the local field strength which is used in the methods of the invention is about 150-500 V/cm. In other embodiments, the local field strength which is used in the methods of the invention is about 250-400 V/cm. In a particular embodiment, local field strength used in the methods of the invention is about 400 V/cm (e.g., in case of CHO cells).

In other embodiments of the invention transfection may be performed using a chemical reagent such as calcium phosphate as precipitant, or cationic lipids and the like, e.g. Lipofectamine™ (INVITROGEN, Carlsbad, Calif.).

Without wishing to be bound by theory, it is contemplated that any suitable method of transfection can be used in the methods of the invention, so long as it is capable of achieving at least 50% or more, or at least 60% or more, or at least 70% or more, or at least 80% or more, or at least 90% or more, or at least 95% or more, or at least 99% or more of the cells being transfected. Additional exemplary methods which may be used in the methods of the invention include, e.g., use of magnetic nanoparticles (e.g., see kits sold by OZ Biosciences) and nanoparticle transfection (e.g., see kits sold by SIGMA-ALDRICH). In a particular embodiment, any method capable of achieving transfection of at least 70% of the cells is used in the methods of the invention. In another embodiment, any method capable of achieving transfection of at least 80% of the cells is used in the methods of the invention.

VII. CELL CULTURE MEDIA

Any suitable culture medium or feed medium suitable for cell growth and protein production may be used in the methods of invention. Suitable culture or feed mediums are chosen for their compatibility with the host cells and polypeptide of interest. Suitable culture or feed mediums are well known in the art and include, but are not limited to, commercial media such as Ham's F10 (SIGMA), Minimal Essential Medium (SIGMA), RPMI-1640 (SIGMA), and Dulbecco's Modified Eagle's Medium SIGMA) are suitable for culturing the animal cells.

In addition, any of the media described in Ham and Wallace, *Meth. Enz.*, 58:44 (1979), Barnes and Sato, *Anal. Biochem.*, 102:255 (1980), U.S. Pat. No. 4,767,704; 4,657,866; 4,927,762; or 4,560,655; WO 90/03430; WO 87/00195; U.S. Pat. No. Re. 30,985; or U.S. Pat. No. 5,122,469, the disclosures of all of which are incorporated herein by reference, may be used as culture or feed media for the host cells. Any of these media may be supplemented with additional components to meet the specific needs of the cells being culture.

VIII. CELL CULTURE METHODS

A polypeptide of interest may be produced using any scheme or routine that may be suitable for a particular cell-type and the particular production plan desired. Therefore, it is contemplated that either a single-step or multiple-step culture procedure may be used in the methods of the invention. For example, in a single-step culture, the cells are inoculated into a culture environment and the subsequent addition of any nutrients or supplements is employed during a single production phase of the cell culture. Alternatively, a multi-stage culture may be used. In the multi-stage culture, cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture. In a particular embodiment, the cells are grown in a multi-stage culture comprising one or more growth stages and a production stage. In some embodiments of the methods of the invention, the growth stage includes from about a 5 L culture volume to about a 200 L culture volume, while the production phase includes about a 15000 L culture volume.

In some embodiments, a higher percentage of viable cells are found in cell culture, thereby contributing to a production of high quality protein at significantly improved yields over other methods well known in the art.

Various cell culture conditions such as, for example, osmolality, temperature and pH may be controlled to obtain optimal protein production (e.g., a high titer) over the duration of the cell culture process and also to reduce batch variability. Such conditions may either be controlled at the growth phase or the production phase of the cell culture process or at both phases.

Additionally, it is contemplated that any suitable mode of culturing cells (e.g., fed-batch or continuous) may be used in the methods of the present invention. In some embodiments of the methods of the present invention, fed-batch or continuous cell culture conditions are used to enhance growth of the mammalian cells in the growth phase of the cell culture. In other embodiments of the methods of the present invention, a bulk cell culture method is devised for cell growth. During fed-batch, or continuous cell culture conditions, the growth phase cells are grown under conditions and for a period of time that is suitable for maximum growth. Culture conditions, such as temperature, pH, osmolality, dissolved oxygen ($DO_2$), and the like, that are optimal for a particular cell type would be apparent to one of ordinary skill in the art or can be readily determined by one of ordinary skill in the art.

Also encompassed by the present invention are methods of culturing cells that produce a resilient cell line, i.e., one that can accommodate variations and still produce improved yields of protein and maintain cell viability, for example, by introducing a nucleotide sequence encoding an anti-apoptotic protein or functional fragment thereof into the cell line and/or contacting the cell line with an isolated anti-apoptotic protein or functional fragment thereof.

In some embodiments, the process results in consistent quality characteristics across multiple cell culture batches. In a particular embodiment, methods of the present invention provide consistent viable cell densities and percentage of viable cells, metabolism consistency, product quality, and protein production levels.

IX. KITS

Also encompassed by the present invention are kits for reducing the levels of one or more contaminants. In some embodiments, a kit according to the present invention comprises: (a) a first nucleic acid molecule comprising one or more DNA elements capable of opening chromatin and/or maintaining chromatin in an open state and a multiple cloning site suitable for cloning a nucleotide sequence encoding a recombinant protein into the molecule; and (b) a second nucleic acid molecule comprising a nucleotide sequence encoding at least one anti-apoptotic protein or a functional fragment thereof operably linked to one or more DNA elements capable of opening chromatin and/or maintaining chromatin in an open state.

In some embodiments, a kit according to the invention includes: (a) a host cell stably transfected with a nucleotide molecule comprising a nucleotide sequence encoding at least one anti-apoptotic protein or a functional fragment thereof operably linked to one or more DNA elements capable of opening chromatin and/or maintaining chromatin in an open state; and (b) a nucleic acid molecule comprising one or more DNA elements capable of opening chromatin and/or maintaining chromatin in an open state operably linked to a multiple cloning site suitable for cloning a nucleotide sequence encoding the recombinant protein, where the nucleic acid molecule is capable of being introduced into the host cell.

In some embodiments, kits featured herein include instructions and/or promotional materials including details regarding using the transfection device or transfection agent. In general, a kit may include one or more of the following along with instructions for use: one or more nucleic acid molecules comprising one or more DNA elements capable of opening chromatin and/or maintaining chromatin in an open state operably linked to a multiple cloning site for cloning a nucleotide sequence encoding a recombinant protein; (b) one or more nucleic acid molecules comprising one or more nucleotide sequences encoding one or more anti-apoptotic proteins or functional fragments thereof operably linked to one or more DNA elements capable of opening chromatin and/or maintaining chromatin in an open state; (c) one or more purified anti-apoptotic proteins or functional fragments thereof; (d) one or more suitable cell lines for introduction of the various nucleic acid molecules; and (e) one or more reagents and/or devices suitable for transfecting the cell lines.

Suitable transfection reagents may include one or more chemical means for transfecting cells with a nucleic such as calcium phosphate, or commercially prepared cationic lipids, e.g. Lipofectamine™ (INVITROGEN, Carlsbad, Calif.). Other commercially available reagents include Silmporter™ (MILLIPORE, Temecula, Calif.); FuGene® (ROCHE, Indianapolis, Ind.). Transfection devices may include an electroporation device such as a controlled electroporation device (EX-CELLIN LIFE SCIENCES, Menlo Park, Calif.). The system may also include a power supply, a computer, e.g. a personal computer including suitable software and hardware for monitoring and or recording data regarding cell viability, and growth, transfection efficiency, pore formation (if electroporation is used) and protein production.

X. PURIFICATION METHODS

Also provided herein are methods of harvesting or purifying a recombinant protein produced using the methods of the invention. In general, any suitable purification scheme known in the art may be used. However, methods described herein simplify the purification process by reducing the levels of one or more contaminants generally present during recombinant protein expression using cell culture methods.

In some embodiments, a method of harvesting a recombinant protein in cell culture does not employ the use of protein A. In some embodiments one or more chromatography steps, e.g. one chromatography step, two chromatography steps, more than two chromatography steps, may be performed to harvest a recombinant product from a cell culture. The chromatography steps may not require the use of stringent wash reagents or elution buffers.

In some embodiments, the harvesting step includes a centrifugation step, where a recombinant protein is found in the cell supernatant in the presence of reduced levels of one or more contaminants.

The harvesting or purification step or steps may be selected by the skilled artisan based upon the product protein. Examples of suitable purification steps for purifying recombinant products according to the invention may include one or more of the following: precipitation of the recombinant protein from the supernatant; crystallization of the of the recombinant protein; high performance tangential flow filtration (HPTFF), flow through chromatography wherein contaminants are retained on a solid support and the recombinant product flows through the chromatography media (e.g. Intercept®)(MILLIPORE CORPORATION, Billerica, Mass.); adsorption purification, e.g. ion exchange chromatography, affinity chromatography.

Other suitable purification steps may be chosen from any chromatography means known in the art, e.g. size exclusion, ion exchange, affinity, reverse phase to name but a few. In certain embodiments the chromatography step may include an ion exchange chromatography step. In other embodiments the chromatography step may not require an affinity chromatography step and the potentially harsh conditions frequently used for elution.

In some embodiments, a recombinant protein is produced in the presence of reduced levels of one or more contaminants, where contaminants are host cell proteins, present in an amount less than about 1000 parts per million (ppm), or less than about 900 ppm, or less than about 800 ppm, or less than about 700 ppm, or less than about 600 ppm, or less than about 500 ppm, or less than about 400 ppm, or less than about 300 ppm, or less than about 200 ppm, or less than about 100 ppm, or less than about 90 ppm, or less than about 80 ppm, or less than about 70 ppm, or less than about 60 ppm, or less than about 50 ppm, or less than about 40 ppm, or less than about 30 ppm, or less than about 20 ppm, or less than about 10 ppm of the total protein.

This invention is further illustrated by the following examples which should not be construed as limiting. The contents of all references, patents and published patent applications cited throughout this application, as well as the Figures, are incorporated herein by reference.

EXAMPLES

Example I

Generation of Stable CHO Cell Clones

Stable clones of CHO cells are generated by transfecting the cells with either an aven gene operably linked to a DNA element capable of opening chromatin and/or maintaining chromatin in an open state, or an E1B-19K gene operably linked to a DNA element capable of opening chromatin and/or maintaining chromatin in an open state (e.g., an extended methylation-free CpG island). In another experiment, stable clones of CHO cells are generated that are transfected with both the aven gene and the E1B-19K gene, each operably linked to a DNA element capable of opening chromatin and/or maintaining chromatin in an open state (e.g., an extended methylation-free CpG island).

Following generation of the stable CHO cells including one or both of the anti-apoptotic genes, the cells are stably transfected with a nucleotide sequence encoding a recombinant protein (e.g., an antibody or a light or heavy chain of an antibody) operably linked to a DNA element capable of opening chromatin and/or maintaining chromatin in an open state (e.g., an extended methylation-free CpG island) and optionally, operably linked to one or more nucleotide sequences which increase secretion of the recombinant protein outside the cell, increase translation of the recombinant protein and increase mRNA stability.

Pools of stably transfected cells are screened instead of individual clones, thereby reducing the time associated with the selection process. Further, no gene amplification is required.

In a control experiment, CHO cells are transfected only with the nucleotide sequence encoding a recombinant protein operably linked to a DNA element capable of opening chromatin and/or maintaining chromatin in an open state and optionally one or more nucleotide sequences discussed above.

Example 2

Evaluation of the Cells for Recombinant Protein Production

Pools of stably transfected CHO cells are subsequently evaluated for the production of the anti-apoptotic genes and the recombinant protein. The expression of the anti-apoptotic genes is evaluated, e.g., by taqman analysis, and the expression of the recombinant protein is evaluated, e.g., by assaying for the binding of the recombinant protein to a known binding partner or any other assay that might be appropriate for the detection of a particular recombinant protein.

Cell supernatant is collected to evaluate for host cell contaminants, e.g., host cell proteins, which can be measured, e.g., using ELISA, or assays available for measuring host cell proteins in CHO cells. Cell supernatants from cells expressing both an anti-apoptotic proteins and the recombinant protein are compared with those from cells expressing only the recombinant protein.

The cell supernatants obtained following centrifugation of cells which express the recombinant protein along with the one or both anti-apoptotic genes include a lower level of host cell contaminants, e.g., host cell proteins, relative to cell supernatants obtained from cells which express the recombinant protein alone.

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and invention are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of enriching for a recombinant protein in cell culture, the method comprising:
   a) transfecting into a host cell, a first nucleic acid molecule comprising a nucleotide sequence encoding a recombinant protein and a second nucleic acid molecule comprising a nucleotide sequence encoding at least one anti-apoptotic protein selected from a protein comprising the amino acid sequence set forth in SEQ ID NO:6, 8 or 10 or a functional fragment thereof having anti-apoptotic activity, wherein both nucleotide sequences are operably linked to a DNA element comprising a nucleotide sequence set forth in SEQ ID NO:1, wherein the DNA element is capable of opening chromatin and/or maintaining the chromatin in an open state; and
   b) culturing the host cell under conditions such that the recombinant protein is produced in the presence of reduced levels of one or more contaminants selected from host cell protein and DNA, thereby to enrich for the recombinant protein in cell culture.

2. The method of claim 1, further comprising the step of harvesting the recombinant protein from the cell culture.

3. The method of claim 2, wherein the levels of one or more contaminants selected from host cell protein and DNA are reduced during the harvesting step.

4. The method of claim 1, wherein both the first nucleic molecule and the second nucleic acid molecule are cloned into a single vector.

5. The method of claim 1, wherein the first nucleic acid molecule and the second nucleic acid molecule are cloned into separate vectors.

6. The method of claim 4 or 5, wherein the vector is a plasmid.

7. The method of claim 4 or 5, wherein the vector is a viral vector.

8. The method of claim 1, wherein the second nucleic acid molecule is introduced before the first nucleic acid molecule.

9. The method of claim 1, wherein the first and the second nucleic acid molecules are introduced simultaneously.

10. The method of claim 1, wherein the first nucleic acid molecule comprises two nucleotide sequences, each encoding a recombinant protein.

11. The method of claim 1, wherein the first nucleic acid molecule further comprises one or more nucleotide sequences chosen from: (a) a nucleotide sequence capable of enhancing translation; (b) a nucleotide sequence capable of increasing secretion; and (c) a nucleotide sequence capable of increasing the mRNA stability, wherein the one or more nucleotide sequences set forth in (a)-(c) are operably linked to the nucleotide sequence encoding the recombinant protein.

12. The method of claim 1, wherein the host cell is a mammalian cell.

13. The method of claim 12, wherein the mammalian cell is chosen from a BHK21 cell, a CHO cell, a CHO-K1 cell, a CHO-DUXX cell, an NSO cell or an Sp2/0 cell.

14. The method of claim 12, wherein the mammalian cell is a Chinese Hamster Ovary Cell (CHO cell).

15. The method of claim 1, wherein the recombinant protein is a therapeutic protein.

16. The method of claim 1, wherein the recombinant protein is an antibody or an antigen-binding fragment thereof.

17. The method of claim 16, wherein the antibody is a monoclonal antibody.

18. The method of claim 1, wherein the host cell is cultured in serum free medium.

19. The method of claim 18, wherein the medium is free of animal products.

20. The method of claim 18, wherein the medium is a protein free media.

21. The method of claim 1, wherein the transfecting step comprises: (a) placing the host cell in an electroporation device comprising a barrier having an opening suitable for receiving the cell; (b) securing the host cell in the opening; (c) contacting the host cell with an electric current such that the current passes through the host cell; (d) monitoring the ratio between the current and voltage in the electroporation device; and (e) adjusting the magnitude of the voltage to optimize electroporation.

22. The method of claim 21, wherein the barrier comprises a dielectric material.

23. The method of claim 1, wherein transfection comprises electroporation.

24. A method of harvesting a recombinant protein expressed according to the method of claim 1, wherein the harvesting step does not comprise the use of protein A and comprises one or more steps chosen from precipitation of the recombinant protein from a supernatant; crystallization; high performance tangential flow filtration (HPTFF), flow through chromatography; adsorption chromatography.

25. The method of claim 24, wherein the adsorption chromatography step is an ion exchange step.

26. The method of claim 24, wherein the harvesting step includes at least one centrifugation step.

27. The method of claim 24, wherein the levels of one or more contaminants are reduced.

28. The method of claim 27, wherein the levels of one or more contaminants selected from host cell protein and DNA are reduced by about 20%, or about 30%, or about 40%, or about 50%, or about 60%, or about 70%, or about 80%, or about 90%, or about 95%, or about 96%, or about 97%, or about 98%, or about 99%, or more, when the recombinant protein is co-expressed with the anti-apoptotic protein or functional fragment thereof having anti-apoptotic activity relative to the levels of the one or more contaminants produced when the recombinant protein is expressed alone.

29. A method of enriching for a recombinant protein in cell culture, the method comprising:
   a) transfecting into a host cell, a first nucleic acid molecule comprising a nucleotide sequence encoding a recombinant protein and a second nucleic acid molecule comprising a nucleotide sequence encoding at least one anti-apoptotic protein selected from a protein comprising the amino acid sequence set forth in SEQ ID NO:6, 8 or 10 or a functional fragment thereof having anti-apoptotic activity, wherein both nucleotide sequences are operably linked to a DNA element consisting of a nucleotide sequence set forth in SEQ ID NO:1, wherein the DNA element is capable of opening chromatin and/or maintaining the chromatin in an open state; and
   b) culturing the host cell under conditions such that the recombinant protein is produced in the presence of reduced levels of one or more contaminants selected from host cell protein and DNA, thereby to enrich for the recombinant protein in cell culture.

* * * * *

SEQUENCE LISTING

```
<160> NUMBER OF SEQ ID NOS: 14

<210> SEQ ID NO 1
<211> LENGTH: 3048
<212> TYPE: DNA
<213> ORGANISM: Mus musculus

<400> SEQUENCE: 1
accactaagc catctctcca gccctgagtc atggttttag tgtgagaggc atcattgaat      60
tttctgagca cggccatcag ggtagctggc acaggtcttc agatacaagg agatagttat     120
aagaaggcag ccatggctgt ggtgcactag aaatggagaa acagcttcat caggtgacag     180
accagtctga ctctgtccca tgattagaag ccatcttgtt acaaggtcaa aataagttca     240
ttcctgtttt ctgtaacact tgggtttgat cctgtcgtca acccattttc tggaatttga     300
catgttccat actccattat accctgactt ccaccctgat aagatgttct gccaagttcc     360
tgtgtagcca acattcccct ggaaatctct cttcccttgg aaaccaccta gtcttagaaa     420
ttttgagtta tataaattcc acttctatgt ttgatgctat tctttaaaac tccactttag     480
ggagatagcc ctgtctgata gaaaataaaa cttgcttaat ttgtctaaaa gattttaagt     540
aatagttttt acttttgttc cgtgggatta gtacagggtg aaacagactc ccgtgtttcc     600
agtgtgaagt gagccacaca ctgcagtaca agttatatca gcaggttctg cctctgcgca     660 atgaacttttt gcttgtgtgg acatcagggt ctgtgtgaag ggaaggtcct atggcctagt     720
tttatactat tcaacagtct gtccccgaag ccctggtgct ttattatttt gacaagcccc     780
tgctgctggt attccaccct gctgcgagtc aaaaagttc ctgtctcgga aaacaaaac      840 aaaacaaaac aaccaaaaaa taatttttt tttcccacag gttctagtgg aggtgctcac     900
taccagaaat cctacaaata agcccatctc atggatcagg gtttaccttt gtaataatat     960
```

-continued

| | |
|---|---|
| taaatctgtg tgcatgtgcg cacgcatgtg ttttatgctt gcatatatgt atacgcagcc | 1020 |
| atggttttct actgtcccac tcactctgta acttactgag ccatccagct ggtcctctaa | 1080 |
| atacatttca atgaaagttt tcattagcgt gaacgtgaag gtggtaaaat ctgttagtgt | 1140 |
| gtgcttatgc ctgtggtttg cacctctagt ctgaaggttg ctcttttcaa attttttatt | 1200 |
| tatttacgtt tttacttctg agtcagaaac tcataaaggc catggcctcg aattcgctat | 1260 |
| gtagtcaacg atgaccttaa acttgtgacc ctctacttcg ttagtgctgg aaccccaagc | 1320 |
| ttgctgagta cagagcactt tcagaccgga actagatgtc tacttcctgt tccgcctaca | 1380 |
| ttacaggttg ctaggttaca ccccccctac gccgttttag acgcaaaact tcatttccca | 1440 |
| tgcaaaactt catttcccat gaacacttgc aagggtcgcc gcgctgcgcg cgtcattgc | 1500 |
| tcccgcccta tacctact tccgcccgcg agccacttcc tttcctttca gcggcgcgcg | 1560 |
| gctgcaagat ggcggtgcag atttccaaga agaggaaggt aagcgtctgg gcccggttcg | 1620 |
| ggagtccgcc gcgggttcta caagtgccag ggaggcctgt ggctccgtaa tcagtcctgt | 1680 |
| ggagcgtctg gggccgcctg ccgtctcttc gagcctcgga tggccgtaga ttgtgtattg | 1740 |
| ggccggagcc gggcgagtgc tgtgtgcctg gcaagggag ggacaaactc ctcgagttct | 1800 |
| ggaccgactc gaacaccggg cgcctccagt tccggactag acacctttga gcgtttcttg | 1860 |
| gtctccataa tagtaatcct gtggcacagt tagagggcgt gtgccatcag atctagtcca | 1920 |
| gtctctttag taagtgaagt ttagcagtcc cttctcttag tcgcgtgatc ctgcaagtgg | 1980 |
| ccatagttga aagcctactt actgactgct gccgtgttca ctcgggaccc ggagctgcag | 2040 |
| cgtccctgtg gttatcattt catggggaa aagtgtgcag gttgccaggt ttagaaatag | 2100 |
| atggtctgtc gtttgtgctt atgcacacag atgataaacc tgttttgagt caggattcct | 2160 |
| ctcctatccg aggtacaact tacagtccca gctgtacatg tgctacttgg agacagattt | 2220 |
| ttctttgtct cttgggtgta gattatgccg tagagccctt cgatgaagag gtgatgacga | 2280 |
| gtctgagtag gaagtgttgt cttttgtccaa gatgcctcac tatgctgcgt tctgtggcac | 2340 |
| agctgaaagc actgtggtca aaagaaaactt cctaaagatg accaagaggc atttgtctga | 2400 |
| gaagggttgc tgcttttctg tagggccatt gggcttgctc tgactaaccc tgtcttcacc | 2460 |
| tcagaggtaa cttgttttcct ttggttcagt ttgtagctga tggcatcttc aaagctgagc | 2520 |
| tgaatgaatt tctcactcgg gagctggctg aagatggcta ctctggagtt gaagtccgag | 2580 |
| ttacaccaac caggacagaa atcattattt tagccaccag gtagaaatac cattgattgt | 2640 |
| cacctgtaaa tattgtgtgt actgagatgc tgtgtaaact tgggccaacc aagcagtaaa | 2700 |
| tctggcctca gtgggtgtaa ctgctttgtt agaactgcat ttgggaagaa cttaccttcc | 2760 |
| atttaacctg tgtgctggcg ttgtggtggg cggcaggtgg gatcttgagt aaatggttgc | 2820 |
| gcttcccctc tacaggacac agaatgttct tggggagaag ggtcgtcgga tcagagagtt | 2880 |
| gaccgcagtt gtccagaagc gctttggctt ccctgaaggc agcgtagagg tgagttcctc | 2940 |
| tgctttatct cccgggggtt ttagactgag ttgggatgtg gcttctgcta tagaattgta | 3000 |
| cttctgaaaa cctgacatgg ccagtgacag tcacaggtac ttgatgct | 3048 |

<210> SEQ ID NO 2
<211> LENGTH: 1558
<212> TYPE: DNA
<213> ORGANISM: Homo sapiens

<400> SEQUENCE: 2

| | |
|---|---|
| ggccctccgc gcctacagct caagccacat ccgaaggggg agggagccgg gagctgcgcg | 60 |

-continued

| | | |
|---|---|---|
| cggggccgcc gggggagggg gtggcaccgc ccacgccggg cggccacgaa gggcggggca | 120 |
| gcgggcgcgc gcccgcgggg gggagggggcc gcgcgccgcg cccgctggga attgggggccc | 180 |
| taggggggagg gcggaggcgc cgacgaccgc ggcacttacc gttcgcggcg tggcgcccgg | 240 |
| tggtccccaa ggggagggaa gggggaggcg gggcgaggac agtgaccgga gtctcctcag | 300 |
| cggtggcttt tctgcttggc agcctcagcg gctggcgcca aaaccggact ccgcccactt | 360 |
| cctcgccccct gcggtgcgag ggtgtggaat cctccagacg ctgggggagg gggagttggg | 420 |
| agcttaaaaa ctagtacccc tttgggacca cttttcagcag cgaactctcc tgtacaccag | 480 |
| gggtcagttc cacagacgcg ggccagggggt gggtcattgc ggcgtgaaca ataatttgac | 540 |
| tagaagttga ttcgggtgtt tccggaaggg gccgagtcaa tccgccgagt tgggggcacgg | 600 |
| aaaacaaaaa gggaaggcta ctaagatttt tctggcgggg gttatcattg gcgtaactgc | 660 |
| agggaccacc tcccggggttg agggggctgg atctccaggc tgcggattaa gccccctcccg | 720 |
| tcggcgttaa tttcaaaactg cgcgaccgtt tctcacctgc cttgcgccaa ggcagggggc | 780 |
| gggaccctat tccaagaggt agtaactagc aggactctag ccttccgcaa ttcattgagc | 840 |
| gcatttacgg aagtaacgtc gggtactgtc tctggccgca agggtgggag gagtacgcat | 900 |
| ttggcgtaag gtggggcgta gagccttccc gccattggcg gcggataggg cgtttacgcg | 960 |
| acggcctgac gtagcggaag acgcgttagt ggggggggaag gttctagaaa agcggcggca | 1020 |
| gcggctctag cggcagtagc agcagcgccg ggtcccgtgc ggaggtgctc ctcgcagagt | 1080 |
| tgtttctcga gcagcggcag ttctcactac agccccagga cgagtccggt tcgtgttcgt | 1140 |
| ccgcggagat cgatctctct catctcgctc ggctgcggga aatcgggctg aagcgactga | 1200 |
| gtccgcgatg gaggtaacgg gttttgaaaatc aatgagttat tgaaaagggc atggcgaggc | 1260 |
| cgttggcgcc tcagtggaag tcggccagcc gcctccgtgg gagagaggca ggaaatcgga | 1320 |
| ccaattcagt agcagtgggg cttaaggttt atgaacgggg tcttgagcgg aggcctgagc | 1380 |
| gtacaaacag cttccccacc ctcagcctcc cggcgccatt tcccttcact gggggtgggg | 1440 |
| gatggggagc tttcacatgg cggacgctgc cccgctgggg tgaaagtggg gcgcggaggc | 1500 |
| gggaattctt attccctttc taaagcacgc tgcttcgggg gccacggcgt ctcctcgg | 1558 |

<210> SEQ ID NO 3
<211> LENGTH: 4180
<212> TYPE: DNA
<213> ORGANISM: Homo sapiens

<400> SEQUENCE: 3

| | | |
|---|---|---|
| ctaaaacagc ttcacatggc ttaaaatagg ggaccaatgt cttttccaat ctaagtccca | 60 |
| tttataataa agtccatgtt ccattttttaa aggacaatcc tttcggttta aaaccaggca | 120 |
| cgattaccca acaactcac aacggtaaag cactgtgaat cttctctgtt ctgcaatccc | 180 |
| aacttggttt ctgctcagaa accctccctc tttccaatcg gtaattaaat aacaaaagga | 240 |
| aaaaacttaa gatgcttcaa ccccgtttcg tgacactttg aaaaaagaat cacctcttgc | 300 |
| aaacacccgc tcccgacccc cgccgctgaa gccggcgtc cagaggccta agcgcgggtg | 360 |
| cccgccccca cccgggagcg cgggcctcgt ggtcagcgca tccgcgggga gaaacaaagg | 420 |
| ccgcggcacg ggggctcaag ggcactgcgc cacaccgcac gcgcctaccc ccgcgcggcc | 480 |
| acgttaactg gcggtcgccg cagcctcggg acagccggcc gcgcgccgcc aggctcgcgg | 540 |
| acgcgggacc acgcgccgcc ctcgggagg cccaagtctc gacccagccc cgcgtggcgc | 600 |
| tggggggaggg ggcgcctccg ccggaacgcg ggtgggggag gggaggggga aatgcgcttt | 660 |

```
gtctcgaaat ggggcaaccg tcgccacagc tccctacccc ctcgagggca gagcagtccc    720
cccactaact accgggctgg ccgcgcgcca ggccagccgc gaggccaccg cccgacccte    780 cactccttcc cgcagctccc ggcgcggggt ccggcgagaa ggggagggga ggggagcgga    840
gaaccgggcc cccgggacgc gtgtggcatc tgaagcacca ccagcgagcg agagctagag    900
agaaggaaag ccaccgactt caccgcctcc gagctgctcc gggtcgcggg tctgcagcgt    960
ctccggccct ccgcgcctac agctcaagcc acatccgaag ggggagggag ccgggagctg   1020
cgcgcggggc cgccgggggg aggggtggca ccgcccacgc cgggcggcca cgaagggcgg   1080
ggcagcgggc gcgcgcgcgg cggggggagg ggccggcgcc gcgcccgctg ggaattgggg   1140 ccctagggg  agggcggagg cgccgacgac cgcggcactt accgttcgcg gcgtggcgcc   1200
cggtggtccc caaggggagg gaaggggggag gcggggcgag gacagtgacc ggagtctcct   1260
cagcggtggc ttttctgctt ggcagcctca gcggctggcg ccaaaaccgg actccgccca   1320
cttcctcgcc cgccggtgcg agggtgtgga atcctccaga cgctggggga ggggagttg    1380 ggagcttaaa aactagtacc cctttgggac cactttcagc agcgaactct cctgtacacc    1440
aggggtcagt tccacagacg cgggccaggg gtgggtcatt gcggcgtgaa caataatttg   1500
actagaagtt gattcgggtg tttccggaag gggccgagtc aatccgccga gttggggcac   1560
ggaaaacaaa aagggaaggc tactaagatt tttctggcgg gggttatcat tggcgtaact   1620
gcagggacca cctcccgggt tgaggggct  ggatctccag gctgcggatt aagcccctcc   1680
cgtcggcgtt aatttcaaac tgcgcgacgt ttctcacctg ccttcgccaa ggcaggggcc   1740
gggaccctat tccaagaggt agtaactagc aggactctag ccttccgcaa ttcattgagc   1800
gcatttacgg aagtaacgtc gggtactgtc tctggccgca agggtgggag gagtacgcat   1860
ttggcgtaag gtgggcgta  gagccttccc gccattggcg gcggataggg cgtttacgcg   1920
acggcctgac gtagcggaag acgcgttagt gggggggaag gttctagaaa agcggcggca   1980
gcggctctag cggcagtagc agcagcgccg ggtcccgtgc ggaggtgctc ctcgcagagt   2040
tgtttctcga gcagcggcag ttctcactac agcgccagga cgagtccggt tcgtgttcgt   2100
ccgcggagat cgatctctct catctcgctc ggctgcggga aatcgggctg aagcgactga   2160
gtccgcgatg gaggtaacgg gtttgaaatc aatgagttat tgaaaagggc atggcgaggc   2220
cgttggcgcc tcagtggaag tcggccagcc gcctccgtgg gagagaggca ggaaatcgga   2280
ccaattcagt agcagtgggg cttaaggttt atgaacgggg tcttgagcgg aggcctgagc   2340
gtacaaacag cttccccacc ctcagcctcc cggcgccatt tcccttcact gggggtgggg   2400
gatggggagc tttcacatgg cggacgctgc cccgctgggg tgaaagtggg gcgcggaggc   2460
gggaattctt attcccttc  taaagcacgc tgcttcgggg gccacggcgt ctcctcggcg   2520
agcgtttcgg cgggcagcag gtcctcgtga gcgaggctgc ggagcttccc ctccccctct   2580
ctcccgggaa ccgatttggc ggccgccatt tcatggctc  gccttcctct cagcgttttc   2640
cttataactc ttttattttc ttagtgtgct ttctctatca agaagtagaa gtggttaact   2700 atttttttt  tcttctcggg ctgttttcat atcgttcga  ggtggatttg gagtgttttg   2760
tgagcttgga tctttagagt cctgcgcacc tcattaaagg cgctcagcct tcccctcgat   2820 gaaatgcgc  cattgcgttc ggaagccaca ccgaagagcg ggaggggggg gtgctccggg   2880
tttgcgggcc cggtttcaga aagatatca  ccacccaggg cgtcgggccg ggttcaatgc   2940
gagccgtagg acaaagaaac catttttatgt ttttcctgtc ttttttttcc tttgagtaac   3000
ggttttatct gggtctgcag tcagtaaaac gacagatgaa ccgcggcaaa ataaacataa   3060
```

```
attggaagcc atcggccacg aggggcaggg acgaaggtgg ttttctgggc gggggaggga   3120
tattcgcgtc agaatccttt actgttctta aggattccgt ttaagttgta gagctgactc   3180
attttaagta atgttgttac tgagaagttt aaccctttacg ggacagatcc atggaccttt   3240
atagatgatt acgaggaaag tgaaataacg attttgtcct tagttatact tcgattaaaa   3300
catggcttca gaggctcctt cctgtaatgc gtatggattg atgtgcaaaa ctgttttggg   3360
cctgggccgc tctgtatttg aactttgtta cttttctcat tttgtttgca atcttggttg   3420
aacattacat tgataagcat aaggtctcaa gcgaagggg tctacctggt tattttttctt   3480 tgaccctaag cacgttttata aaataacatt gtttaaaatc gatagtggac atcgggtaag   3540
tttggataaa ttgtgaggta agtaatgagt ttttgctttt tgttagtgat tgtaaaaact   3600
tgttataaat gtacattatc cgtaatttca gtttagagat aacctatgtg ctgacgacaa   3660
ttaagaataa aaactagctg aaaaaatgaa ataactatc gtgacaagta accatttcaa   3720
aagactgctt tgtgtctcat aggagctagt ttgatcattt cagttaattt tttctttaat   3780
ttttacgagt catgaaaact acaggaaaaa aaatctgaac tgggttttac cactacttttt  3840 taggagttgg gagcatgcga atggagggag agctccgtag aactgggatg agagcagcaa   3900
ttaatgctgc ttgctaggaa caaaaaataa ttgattgaaa attacgtgtg acttttttagt  3960 ttgcattatg cgtttgtagc agttggtcct ggatatcact ttctctcgtt tgaggttttt   4020
taacctagtt aacttttaag acaggtttcc ttaacattca taagtgccca gaatacagct   4080
gtgtagtaca gcatataaag atttcagctc tgaggttttt cctattgact tggaaaattg   4140
ttttgtgcct gtcgcttgcc acatggccaa tcaagtagct                          4180

<210> SEQ ID NO 4
<211> LENGTH: 8285
<212> TYPE: DNA
<213> ORGANISM: Homo sapiens

<400> SEQUENCE: 4
agcttcaatg tttttagcac cctctgtgtg gaggaaaata atgcagatta ttctaattag     60
tgtaatatct aaccacatta aaatatatta catagtaaac tacactccat aattttataa    120
atttgactcc ccagggtaat aaactagtct ctagtctgct caccttcaac tgtacaataa    180
agtcttggtt cttttgaaat agacctcaaa tgagacacct aaaattcaaa gtgtctttac    240
atttaaagac acctacagga aagcaggtaa aagagccagg ttaaaaacaa attctaaaac    300
cacttagctg cagttaaaca tatagtaaag atgcactaaa gtttcttact ctgtaaatcc    360
cttccacttc aggaaatatt ccactttccc attcactaca cgtcgatcta gtacttttc     420 cacgacaaat tcttcaggct ctgcctcttc aacttttta ctctttccat tctgtttttt     480
tcccattttt tgctaaaata aaacaaaaga gaaattaaga atattcctc ttgaattttg     540 agcacatttt caaggctcaa ttgcttatat tattatcaca ttcgacataa attttttactt   600 ctatatccca gggcagacac cttctggaaa gattaaaagt caacagacaa taaaataaaa    660
gaatgcttta tcttgttcat ttagttcaaa cttacaaccc accaccaaaa taatacaata    720
aaaaaacact atctggaaac agttattttt ttccagtctt tttttttgag acagggtctc    780
acactcttgt cgcccaggct ggagtgcagt ggcgtgatct cagctcactg caacctccgc    840 ctcccccaggt tcaagcagtt ctcatgcctc agcctccaga gtagctggga ttataggcgg   900
atgccaccat gccgggctaa ttttttttgt gttttattta gaaacagggt ttcaccatgt    960
tgaccaggct ggtctcaaac tcctgacctg aagtgattca ccagcctggg cctcccaaag   1020
```

```
tgctggcatt acaggcgtga gccactgcgc ccggccctgt agtcttaaaa gaccaagttt   1080
actaattttc actcatttta acaacactgc aacaaacaac tatgcaggaa gtacctaaag   1140
ggtgatccag agaagcaagt agtagtgaca ggtcttaggt gaacctatga cagaccttgt   1200
atccaccccc agatggtaaa agccccagcc cccttctcaa ttcaaatatt aatgtcaaaa   1260
gcatcaatga tacagagaaa agataaatgc agaatgaaaa catggttcaa atcctgata   1320 ccaactgcag ggtcaactat agagaccact aggaggttca attaaaggac aagattattt   1380
ttccataatc tctgtagata atatttccta ccacttagaa caaaactata aagctatcac   1440
ttcaagagac caacattaca aatttatttt aattccctaa ggtgaaaaaa atccttcctt   1500
cctggtttct caagagaaag tctatactgg taaccaaatt cactttaaac aggcattttc   1560
tttggtatga cactatttaa gagaagcagg aaaccaacgt gaaccagctc tttccaatgg   1620
ctcaagattt cctatgagag gactaaaaat ggggaaaatt tttatgagag gattaaaaat   1680
gggggaaaaa aaaccctgaa atggttaatc agaagatcct atgggctgag aaggaatcca   1740
tcttaacatt tcatcttaaa gcaaatgcta ttgccggggg cagtggctca tgcctgtaat   1800
cccagcactt tgggaggccg aggtgggcag atcatctgag gtcaggagtt tgagaccagc   1860
ctgaccaaca tggagaaacc ccgtttctac taaaaataca aaattagcca ggcatagtgg   1920
tgcatgcctg taatcccagc tacttgggag gctgaggcag gagaactgct tgaacccagg   1980
aggcttaagt tgcggtgagc caagatcacg ccattgcact ctagcctgga caacaagaga   2040
aaaactctgt ctcaaaaaaa cacaaaaaca aaaaacccaa atactattta aaaaagataa   2100
accttaattg ctcaatcatt aaagccatcc cacaagtaaa gcagcaagca gaaaaaagtt   2160
aagaacacct caaggctaca gaaggacatt tcaagctatg caggcatatg aagtgtgcag   2220
acagatatgt aagaaaggcc tcaagactgc aaaagggcat tcaagctat gcaagcatat   2280 aggtaacaca tacacacaca caaaataaaa tcccctgaaa tacaaaaaca tgcagcaaac   2340
acctgacgtt tttggatacc atttctaagt caggtgttat gattctcatt agtcaagata   2400
cttgagtact gggcccaaac agctttctgc cactgtacag tacaagaagg taggaataat   2460
ggtgggagga gcaaagacaa actgtaatag acagaagtgt atcagatacc tatactacat   2520
gaaaaacaaa acagctactg ccacaaaggg agaaggctaa caaaataaag tcaacaataa   2580
atacagaaaa tgaaaggat acacactaag gtttacaaaa aaaaaaaggc agacaaaatg   2640
ccatacagta ttcattcact actatggcat tcataagcta gtttcaaatg ctcactattt   2700
tcttttatag tatatatttg ccttaaccca gcacttttt ccaaaagtgg atgagtcaaa   2760
ataaatttcc cattatttaa gtgaaattaa cagcacacat atctcacaac actaatgaat   2820
ttttaaaatg gaaagttaag aactttaaa gtggccaacc tgtgatcctt cacaaaataa   2880
actaaataca ataacagacc caaaggcta tcaattgcgt gcaaaacaa cttctgtttt   2940 ccagggtaaa cagaatctaa tgcagaatct aatgcagggt aaacagactt aatgcagaat   3000
ctaatgatgg cacaaattaa aaatcactaa cgtgcccttt ttagtgtgaa acccagagag   3060
agcacataca agccaaaaac aaatgctta ttttacctag gagacattaa cattcaccttt   3120 tacgtgttta agattaatgc aatgttaaat attgtgaaaa ctgtaacttt gaatttcatg   3180 attttttatgt gaatattcca gggttaaaa aaacttgtaa catgacatgg ctgaataaga   3240
taaaaaaaaa atctagcctt tctcccttc tggctcatat ttgcgatttc gatcatttg   3300 tttaaaaaac aaaacactgc aatgaattaa acttaatatt cttctatgtt ttagagtaag   3360
ttaaaacaag ataaagtgac caaagtaatt tgaaagattc aatgactttt gctccaacct   3420
```

```
aggtgcacaa ggtaccttgt tctttaaatt gggctttaat gaaaatactt ctccagaatt    3480
ctggggattt aagaaaaatt atgccaacca acaagggctt taccatttta tgtaacattt    3540
ttcaacgctg caaaaatgtg tgtatttcta tttgaagata aaatcctca gcaaaatcca     3600 cattgcactg tccttcaaag attagccttc tttgaactag ttaagacact attaagccaa    3660
gccagtatct ccctgtaatg aattcgtttt tctcttaatt ttcccctgta atttacactg    3720
ggagagctgg gaaatatgtg gatgtaaatt tctcagccac agagatgcaa agttatactg    3780
tggggaaaaa aaacttgagt taaatcctta catattttag gttttcatta acttaccaat    3840
gtagttttgt tggaggccat tttttttatt gcagacttga agagctatta ctagaaaaat    3900
gcatgacagt taaggtaagt ttgcatgaca caaaaaaggt aactaaatac aaattctgtt    3960
tggattccaa cccccaagta gagagcgcac actttcaaac gtgaatacaa atccagagta    4020
gatctgcgct cctacctaca ttgcttatga tgtacttaag tacgtgtcct aaccatgtga    4080
gtctagaaag actttactgg ggatcctggt acctaaaaca gcttcacatg gcttaaaata    4140
ggggaccaat gtcttttcca atctaagtcc catttataat aaagtccatg ttccattttt    4200
aaaggacaat ccttcggtt taaaaccagg cacgattacc caaacaactc acaacgtaa     4260 agcactgtga atcttctctg ttctgcaatc ccaacttggt ttctgctcag aaaccctccc    4320
tctttccaat cggtaattaa ataacaaaag gaaaaaactt aagatgcttc aaccccgttt    4380
cgtgacactt tgaaaaaga atcacctctt gcaaacaccc gctcccgacc ccgccgctg     4440 aagcccggcg tccagaggcc taagcgcggg tgcccgcccc cacccgggag cgcgggcctc    4500
gtggtcagcg catccgcggg gagaaacaaa ggccgcggca cggggggctca agggcactgc   4560 gccacaccgc acgcgcctac ccccgcgcgg ccacgttaac tggcggtcgc cgcagcctcg    4620
ggacagccgg ccgcgcgccg ccaggctcgc ggacgcggga ccacgcgccg ccctccggga    4680
ggcccaagtc tcgacccagc cccgcgtggc gctgggggag ggggcgcctc cgccggaacg    4740
cgggtggggg aggggagggg gaaatgcgct ttgtctcgaa atggggcaac cgtcgccaca    4800
gctccctacc ccctcgaggg cagagcagtc cccccactaa ctaccgggct ggccgcgcgc    4860
caggccagcc gcgaggccac cgcccgaccc tccactcctt cccgcagctc ccggcgcggg    4920
gtccggcgag aaggggaggg gaggggagcg gagaaccggg cccccgggac gcgtgtggca    4980
tctgaagcac caccagcgag cgagagctag agagaaggaa agccaccgac ttcaccgcct    5040
ccgagctgct ccgggtcgcg ggtctgcagc gtctccggcc ctccgcgcct acagctcaag    5100
ccacatccga agggggaggg agccgggagc tgcgcgcggg gccgccgggg ggaggggtgg    5160
caccgcccac gccgggcggc cacgaagggc ggggcagcgg gcgcgcgcgc ggcgggggga    5220
ggggccggcg ccgcgcccgc tgggaattgg ggccctaggg ggagggcgga ggcgccgacg    5280
accgcggcac ttaccgttcg cggcgtggcg cccggtggtc cccaagggga gggaaggggg    5340
aggcggggcg aggacagtga ccggagtctc ctcagcggtg gctttctgc ttggcagcct     5400 cagcggctgg cgccaaaacc ggactccgcc cacttcctcg cccgccggtg cgagggtgtg    5460
gaatcctcca gacgctgggg gagggggagt tgggagctta aaaactagta ccccctttggg   5520 accactttca gcagcgaact ctcctgtaca ccagggtgtca gttccacaga cgcgggccag   5580
gggtgggtca ttgcggcgtg aacaataatt tgactagaag ttgattcggg tgtttccgga    5640
aggggccgag tcaatccgcc gagttgggc acggaaaaca aaaagggaag gctactaaga     5700
tttttctggc ggggttatc attggcgtaa ctgcagggac cacctcccgg gttgaggggg     5760
ctggatctcc aggctgcgga ttaagcccct cccgtcggcg ttaatttcaa actgcgcgac    5820
```

-continued

```
gtttctcacc tgccttcgcc aaggcagggg ccgggacect attccaagag gtagtaacta   5880
gcaggactct agccttccgc aattcattga gcgcatttac ggaagtaacg tcgggtactg   5940
tctctggccg caagggtggg aggagtacgc atttggcgta aggtggggcg tagagccttc   6000
ccgccattgg cggcggatag ggcgtttacg cgacggcctg acgtagcgga agacgcgtta   6060
gtgggggga aggttctaga aaagcggcgg cagcggctct agcggcagta gcagcagcgc   6120
cgggtcccgt gcgaggtgc tcctcgcaga gttgtttctc gagcagcggc agttctcact   6180
acagcgccag gacgagtccg gttcgtgttc gtccgcggag atctctctca tctcgctcgg   6240
ctgcgggaaa tcgggctgaa gcgactgagt ccgcgatgga ggtaacgggt ttgaaatcaa   6300
tgagttattg aaaagggcat ggcgaggccg ttggcgcctc agtggaagtc ggccagccgc   6360
ctccgtggga gagaggcagg aaatcggacc aattcagtag cagtgggget taaggtttat   6420
gaacggggtc ttgagcggag gcctgagcgt acaaacagct tccccaccct cagcctcccg   6480
gcgccatttc ccttcactgg gggtggggga tggggagctt tcacatggcg gacgctgccc   6540
cgctggggtg aaagtggggc gcggaggcgg gaattcttat tccctttcta aagcacgctg   6600
cttcgggggc cacggcgtct cctcggcgag cgtttcggcg ggcagcaggt cctcgtgagc   6660
gaggctgcgg agcttcccct cccctctct cccgggaacc gatttggcgg ccgccatttt   6720
catggctcgc cttcctctca gcgttttcct tataactctt ttattttctt agtgtgcttt   6780
ctctatcaag aagtagaagt ggttaactat ttttttttc ttctcgggct gttttcatat   6840
cgtttcgagg tggatttgga gtgttttgtg agcttggatc tttagagtcc tgcgcacctc   6900
attaaaggcg ctcagccttc ccctcgatga aatggcgcca ttgcgttcgg aagccacacc   6960
gaagagcggg gaggggggt gctccggggtt tgcgggcccg gtttcagaga agatatcacc   7020
acccagggcg tcgggccggg ttcaatgcga gccgtaggac aaagaaacca ttttatgttt   7080
ttcctgtctt tttttttcctt tgagtaacga ttttatctgg gtctgcagtc agtaaaacga   7140
cagatgaacc gcggcaaaat aaacataaat tggaagccat cggccacgag gggcagggac   7200
gaaggtggtt ttctgggcgg gggagggata ttcgcgtcag aatcctttac tgttcttaag   7260
gattccgttt aagttgtaga gctgactcat tttaagtaat gttgttactg agaagtttaa   7320
cccttacggg acagatccat ggacctttat agatgattac gaggaaagtg aataacgat   7380
tttgtcctta gttatacttc gattaaaaca tggcttcaga ggctccttcc tgtaatgcgt   7440
atggattgat gtgcaaaact gttttgggcc tgggccgctc tgtatttgaa ctttgttact   7500
tttctcattt tgtttgcaat cttggttgaa cattacattg ataagcataa ggtctcaagc   7560
gaaggggtc tacctggtta ttttttcttg accctaagca cgtttataaa ataacattgt   7620
ttaaaatcga tagtggacat cgggtaagtt tggataaatt gtgaggtaag taatgagttt   7680
ttgcttttg ttagtgattt gtaaaacttg ttataaatgt acattatccg taatttcagt   7740
ttagagataa cctatgtgct gacgacaatt aagaataaaa actagctgaa aaatgaaaa   7800
taactatcgt gacaagtaac catttcaaaa gactgctttg tgtctcatag gagctagttt   7860
gatcatttca gttaatttt tctttaattt ttacgagtca tgaaaactac aggaaaaaaa   7920
atctgaactg ggttttacca ctacttttta ggagttggga gcatgcgaat ggagggagag   7980
ctccgtagaa ctgggatgag agcagcaatt aatgctgctt gctaggaaca aaaataatt   8040
gattgaaaat tacgtgtgac tttttagttt gcattatgcg tttgtagcag ttggtcctgg   8100
atatcacttt ctctcgtttg aggtttttta acctagttaa ctttaagac aggtttcctt   8160
aacattcata agtgcccaga atacagctgt gtagtacagc atataaagat ttcagctctg   8220
```

```
aggtttttcc tattgacttg gaaaattgtt ttgtgcctgt cgcttgccac atggccaatc    8280
aagta                                                                8285

<210> SEQ ID NO 5
<211> LENGTH: 1551
<212> TYPE: DNA
<213> ORGANISM: Homo sapiens

<400> SEQUENCE: 5
gggcgtctcc gccgcagctc ggctcccgcg cgctcagcac cgccagcggc ggccagatgc     60
aggcggagcg aggagctcgg ggaggccgtg ggcggcggcc aggccgcggc cggcctggcg    120
gagatcgcca cagcgagcgg cccggagccg cagcggcggt agccagaggc ggcggcggag    180
gcggcggcgg ggacggaggc ggacgccggg gccgtggccg tggccgggc ttccgcggcg     240 ctcgcggagg ccgaggagga ggaggcgccc cgcgaggcag ccgccgggag ccgggaggct    300
ggggcgcagg ggccagcgcg ccggttgaag atgacagcga tgcagagacc tatggagaag    360
agaatgatga acagggaaat tattctaaaa gaaagattgt ctctaactgg gatcgatatc    420
aagatattga aaaagaggtc aataatgaaa gtggagagtc acagagggga acagatttca    480
gtgtcctcct tagctctgca ggggactcat tctcacagtt ccggtttgct gaggagaaag    540
aatgggatag tgaagcttct tgtccaaaac agaattcagc attttatgtg gatagtgagt    600
tattggttcg agcccttcaa gagctgcctc tctgcctccg actcaacgtt gctgccgaac    660
tggtccaggg tacagttcct ttagaggttc ctcaggtgaa accaaagaga actgatgatg    720
gcaagggatt agggatgcag ttaaaggggc ccttggggcc tggaggaagg gggcccatct    780
ttgagctgaa atctgtggct gctggctgcc ctgtgttgct gggcaaagac aacccaagcc    840
cgggtccttc aagggattct cagaaaccca cttcccccact gcagtcagca ggagaccatt    900
tggaagaaga actagatctg ttgcttaatt tagatgcacc tataaaagag ggagataaca    960
tcttaccaga tcagacgtct caggacctga atccaaggga agatggggag gtggtccaag   1020
aggaagaagt ttgtgcaaaa ccatctgtga ctgaagaaaa aaacatggaa cctgagcaac   1080
caagtacctc caaaaatgtt accgaggaag agctggaaga ctggttggac agcatgattt   1140
cctaaaaagg ggaaaaaaag tgcctgaagc aaatcttggt tgccttctaa cggcaggtgg   1200
gcataaggct gtccttcagg accagccagt ttacaagcat gtctcaagct agtgtgttcc   1260
attatgctca cagcagtaaa tgcctacctc tgtgtttgac atctgaaaga atacattgaa   1320
gcagcttgtt gcatttgttt ttctggctta gtaatctaat agatttcctt aagggcagga   1380
gatagactct ggcccttgtt tctagcctcc ttccttgcag tgtttacaac atagccagtg   1440
tttacagcat agcagatgct gctgctgatt aagagaatag atgcaaacaa ggcatgcatt   1500
tggccaaaat aaacaaatgc tggtctgtcc aaaaaaaaaa aaaaaaaaaa a            1551

<210> SEQ ID NO 6
<211> LENGTH: 362
<212> TYPE: PRT
<213> ORGANISM: Homo sapiens

<400> SEQUENCE: 6

Met Gln Ala Glu Arg Gly Ala Arg Gly Gly Arg Gly Arg Arg Pro Gly
 1               5                  10                  15

Arg Gly Arg Pro Gly Gly Asp Arg His Ser Glu Arg Pro Gly Ala Ala
            20                  25                  30

Ala Ala Val Ala Arg Gly Gly Gly Gly Gly Gly Gly Asp Gly Gly
        35                  40                  45
```

Gly Arg Arg Gly Arg Gly Arg Gly Phe Arg Gly Ala Arg Gly
        50                  55                  60

Gly Arg Gly Gly Gly Ala Pro Arg Gly Ser Arg Arg Glu Pro Gly
 65                  70                  75                  80

Gly Trp Gly Ala Gly Ala Ser Ala Pro Val Glu Asp Asp Ser Asp Ala
                 85                  90                  95

Glu Thr Tyr Gly Glu Glu Asn Asp Gln Gly Asn Tyr Ser Lys Arg
                100                 105                 110

Lys Ile Val Ser Asn Trp Asp Arg Tyr Gln Asp Ile Glu Lys Glu Val
            115                 120                 125

Asn Asn Glu Ser Gly Glu Ser Gln Arg Gly Thr Asp Phe Ser Val Leu
130                 135                 140

Leu Ser Ser Ala Gly Asp Ser Phe Ser Gln Phe Arg Phe Ala Glu Glu
145                 150                 155                 160

Lys Glu Trp Asp Ser Glu Ala Ser Cys Pro Lys Gln Asn Ser Ala Phe
                165                 170                 175

Tyr Val Asp Ser Glu Leu Leu Val Arg Ala Leu Gln Glu Leu Pro Leu
            180                 185                 190

Cys Leu Arg Leu Asn Val Ala Ala Glu Leu Val Gln Gly Thr Val Pro
        195                 200                 205

Leu Glu Val Pro Gln Val Lys Pro Lys Arg Thr Asp Asp Gly Lys Gly
    210                 215                 220

Leu Gly Met Gln Leu Lys Gly Pro Leu Gly Pro Gly Gly Arg Gly Pro
225                 230                 235                 240

Ile Phe Glu Leu Lys Ser Val Ala Ala Gly Cys Pro Val Leu Leu Gly
                245                 250                 255

Lys Asp Asn Pro Ser Pro Gly Pro Ser Arg Asp Ser Gln Lys Pro Thr
            260                 265                 270

Ser Pro Leu Gln Ser Ala Gly Asp His Leu Glu Glu Leu Asp Leu
        275                 280                 285

Leu Leu Asn Leu Asp Ala Pro Ile Lys Glu Gly Asp Asn Ile Leu Pro
    290                 295                 300

Asp Gln Thr Ser Gln Asp Leu Lys Ser Lys Glu Asp Gly Glu Val Val
305                 310                 315                 320

Gln Glu Glu Glu Val Cys Ala Lys Pro Ser Val Thr Glu Glu Lys Asn
                325                 330                 335

Met Glu Pro Glu Gln Pro Ser Thr Ser Lys Asn Val Thr Glu Glu Glu
            340                 345                 350

Leu Glu Asp Trp Leu Asp Ser Met Ile Ser
        355                 360

<210> SEQ ID NO 7
<211> LENGTH: 1234
<212> TYPE: DNA
<213> ORGANISM: Mus musculus

<400> SEQUENCE: 7
gtcgcgcgtt ctgctcgccg gcggcctcat gcaggctgag cgcggggcta ggggcggccg     60
cgggcggcgg ggaggccggg agcggcccgg aggggaccga gagccggtcg gggcagcgac    120
ggcgctggcg agaggaggct gcgggacgg aggcggccgg cggggccgag gccggggctt    180
ccgccgaggc cgaggaggtg gcggcctgcg aggcggccgc tgggagcctg gaggccgggg    240
cggcggagcc agcactcggg tggaagaaga cagcgattca gagacctatg gagaagagaa    300
tgatgagcaa ggaaattttt ctagaagaaa gattgtctcc aactgggatc gctatcaaga    360

```
tactgaaaag gaggtcaatg gtgaaagtgg agaatctcag cggggcacag acttcagtgt    420
cctcctgagc tctgcagggg actccttttc acagttccga tttgctgagg agaaagaatg    480
ggatggtgaa acttcatgtc caaaacagaa ttcagcactc tacgtggaca gtgagtcact    540
ggttcgagcc cttgagcagc tgcctcttgc agtcaggctt aatgttgctt cagaattgat    600
ccagaccaca attcctttag aacttccaca ggtgaaacca aggagaaacg atgatggcaa    660
ggagctgggc atgcatttaa ggggacccat ctctgagctc agatctgctg ctggtgcttg    720
ccccaggtct ctgggcagag gcagtctaag gcaaagccct ttagaaggtt tgcagaaagc    780
acctacccca acacagtcag tggcagacca cctggaagaa gaactagata tgttgctgca    840
tttagatgca cctgtgcaag aggaaggcat tatctctcca gaccagacat ctcgggacca    900
ggaaccagaa aaagatgggc aggtagccca ggaggaaaca ggtcctgaaa aaccttctgt    960
gaccagagag aagaatgtgg aacctgagca gccaagcaca tcgaagaatg tcaccgagga   1020
agagctggag gactggctgg acagcatgat ttcctgaagc ggggtcaagg gggaagagtg   1080
cctgaagcaa atgctggttg ccttctgtgt aatgagcccg tcttgtgagg acgggctcgt   1140
ttaccagcta ccccatgcta acacgtcctg ttatgcttac agcagccaac acctacctct   1200
gtgtttgatg gcatctgaat atatgtatga ggcc                                1234

<210> SEQ ID NO 8
<211> LENGTH: 342
<212> TYPE: PRT
<213> ORGANISM: Mus musculus

<400> SEQUENCE: 8

Met Gln Ala Glu Arg Gly Ala Arg Gly Gly Arg Gly Arg Arg Gly Gly
  1               5                  10                  15

Arg Glu Arg Pro Gly Gly Asp Arg Glu Pro Val Gly Ala Ala Thr Ala
                 20                  25                  30

Leu Ala Arg Gly Gly Cys Gly Asp Gly Gly Arg Arg Gly Arg Gly
             35                  40                  45

Arg Gly Phe Arg Arg Gly Arg Gly Gly Gly Leu Arg Gly Gly Arg
         50                  55                  60

Trp Glu Pro Gly Gly Arg Gly Gly Gly Ala Ser Thr Arg Val Glu Glu
 65                  70                  75                  80

Asp Ser Asp Ser Glu Thr Tyr Gly Glu Glu Asn Asp Glu Gln Gly Asn
                 85                  90                  95

Phe Ser Arg Arg Lys Ile Val Ser Asn Trp Asp Arg Tyr Gln Asp Thr
            100                 105                 110

Glu Lys Glu Val Asn Gly Glu Ser Gly Glu Ser Gln Arg Gly Thr Asp
        115                 120                 125

Phe Ser Val Leu Leu Ser Ser Ala Gly Asp Ser Phe Ser Gln Phe Arg
    130                 135                 140

Phe Ala Glu Glu Lys Glu Trp Asp Gly Glu Thr Ser Cys Pro Lys Gln
145                 150                 155                 160

Asn Ser Ala Leu Tyr Val Asp Ser Glu Ser Leu Val Arg Ala Leu Glu
                165                 170                 175

Gln Leu Pro Leu Ala Val Arg Leu Asn Val Ala Ser Glu Leu Ile Gln
            180                 185                 190

Thr Thr Ile Pro Leu Glu Leu Pro Gln Val Lys Pro Arg Arg Asn Asp
        195                 200                 205

Asp Gly Lys Glu Leu Gly Met His Leu Arg Gly Pro Ile Ser Glu Leu
    210                 215                 220
```

Arg Ser Ala Ala Gly Ala Cys Pro Arg Ser Leu Gly Arg Gly Ser Leu
225                 230                 235                 240

Arg Gln Ser Pro Leu Glu Gly Leu Gln Lys Ala Pro Thr Pro Thr Gln
            245                 250                 255

Ser Val Ala Asp His Leu Glu Glu Leu Asp Met Leu Leu His Leu
        260                 265                 270

Asp Ala Pro Val Gln Glu Glu Gly Ile Ile Ser Pro Asp Gln Thr Ser
        275                 280                 285

Arg Asp Gln Glu Pro Glu Lys Asp Gly Gln Val Ala Gln Glu Glu Thr
290                 295                 300

Gly Pro Glu Lys Pro Ser Val Thr Arg Glu Lys Asn Val Glu Pro Glu
305                 310                 315                 320

Gln Pro Ser Thr Ser Lys Asn Val Thr Glu Glu Leu Glu Asp Trp
            325                 330                 335

Leu Asp Ser Met Ile Ser
            340

<210> SEQ ID NO 9
<211> LENGTH: 504
<212> TYPE: DNA
<213> ORGANISM: Homo sapiens

<400> SEQUENCE: 9
atggagttgt ggagtgagtt acaaagttat cagaacctcc gacgcttgct ggagttggct      60
tctgccagaa cttccagctg ttggagaatc ctttttggct caactttaac taatgtaatc     120
tatagagcta aggaggagta ctcttcgcgg tttgctgacc ttttgtcgca taaccctgga     180
atttttgctt ctttgaattt ggggcatcac tcatttttc aagaaattgt gatcagaaat      240 ttagatttt cttctcctgg ccgtacggtt tctgggcttg cttttatttg ttttatattg      300
gatcaatgga gcgcccaaac tcatctgtcg cagggttata ctctggatta catggcaatg     360
gctctgtgga gaaccttgct acggaggaag agggtcttag gttgcttgcc ggcgcagcgt     420
ccgcacggtt tggatccagt gcaggaagag gaggaggagg aggagaacct gagggccggc     480
ctggacccct caacggaatt gtaa                                            504

<210> SEQ ID NO 10
<211> LENGTH: 167
<212> TYPE: PRT
<213> ORGANISM: Homo sapiens

<400> SEQUENCE: 10

Met Glu Leu Trp Ser Glu Leu Gln Ser Tyr Gln Asn Leu Arg Arg Leu
1               5                   10                  15

Leu Glu Leu Ala Ser Ala Arg Thr Ser Ser Cys Trp Arg Ile Leu Phe
            20                  25                  30

Gly Ser Thr Leu Thr Asn Val Ile Tyr Arg Ala Lys Glu Glu Tyr Ser
        35                  40                  45

Ser Arg Phe Ala Asp Leu Leu Ser His Asn Pro Gly Ile Phe Ala Ser
    50                  55                  60

Leu Asn Leu Gly His His Ser Phe Phe Gln Glu Ile Val Ile Arg Asn
65                  70                  75                  80

Leu Asp Phe Ser Ser Pro Gly Arg Thr Val Ser Gly Leu Ala Phe Ile
                85                  90                  95

Cys Phe Ile Leu Asp Gln Trp Ser Ala Gln Thr His Leu Ser Gln Gly
            100                 105                 110

```
Tyr Thr Leu Asp Tyr Met Ala Met Ala Leu Trp Arg Thr Leu Leu Arg
        115                 120                 125

Arg Lys Arg Val Leu Gly Cys Leu Pro Ala Gln Arg Pro His Gly Leu
    130                 135                 140

Asp Pro Val Gln Glu Glu Glu Glu Glu Glu Asn Leu Arg Ala Gly
145                 150                 155                 160

Leu Asp Pro Ser Thr Glu Leu
            165

<210> SEQ ID NO 11
<211> LENGTH: 449
<212> TYPE: DNA
<213> ORGANISM: Gallus gallus

<400> SEQUENCE: 11
aagcttcttt ggaaatacac cgacttgatt gaagtctctt gaagatagta acagtactt      60 acctttgatc ccaatgaaat cgagcatttc agttgtaaaa gaattccgcc tattcatacc    120
atgtaatgta attttacacc cccagtgctg acactttgga atatattcaa gtaatagact    180
ttggcctcac cctcttgtgt actgtatttt gtaatagaaa atattttaaa ctgtgcatat    240
gattattaca ttatgaaaga acattctgc tgatcttcaa atgtaagaaa atgaggagtg    300
cgtgtgcttt ataaataca agtgattgca aattagtgca ggtgtcctta aaaaaaaaa      360 aaagtaatat aaaaaggacc aggtgtttta caagtgaaat acattcctat ttggaaaaca    420
gttacatttt tatgaagatt accagcgct                                      449

<210> SEQ ID NO 12
<211> LENGTH: 660
<212> TYPE: DNA
<213> ORGANISM: Gallus gallus

<400> SEQUENCE: 12
gcgctgctga ctttctaaac ataaggctgt attgtcttcc tgtaccattg catttcctca     60
ttcccaattt gcacaaggat gtctgggtaa actattcaag aaatggcttt gaaatacagc    120
atgggagctt gtctgagttg aatgcagag ttgcactgca aaatgtcagg aaatggatgt     180
ctctcagaat gcccaactcc aaaggattta tatgtgtata agtaagcag tttcctgatt      240 ccagcaggcc aaagagtctg ctgaatgttg cgttgccgga gacctgtatt ctcaacaag     300 gtaagatggt atcctagcaa ctgcggattt taatacattt tcagcagaag tacttagtta    360
atctctacct ttagggatcg tttcatcatt tttagatgtt atacttgaaa tactgcataa    420
cttttagctt tcatgggttc cttttttttca gcctttagga gactgttaag caatttgctg    480
tccaactttt gtgttggtct taaactgcaa tagtagttta ccttgtattg aagaaataaa    540
gaccattttt atattaaaaa atactttgt ctgtcttcat tttgacttgt ctgatatcct     600
tgcagtgctc attatgtcag ttctgtcaga tattcacaca tcaaaactta acgtgagctc    660

<210> SEQ ID NO 13
<211> LENGTH: 1668
<212> TYPE: DNA
<213> ORGANISM: Gallus gallus

<400> SEQUENCE: 13
ggatccataa tataactgta ccaggttttg gtttattaca tgtgactgac ggcttcctat      60
gcgtgctcag aaaacggcag ttgggcactg cactgcccgg tgatggtgcc acggtggctc    120
ctgccgcctt ctttgatatt cactctgttg tatttcatct cttgttgccg atgaaaggat    180
```

```
ataacagtct ctgaggaaat acttggtatt tcttctgatc agcgttttta taagtaatgt    240
tgaatattgg ataaggctgt gtgtcctttg tcttgggaga caaagcccac agcaggtggt    300
ggttgggtgg tggcagctca gtgacaggag aggttttttt gcctgttttt tttgttgttt    360
ttttttttta agtaaggtgt tcttttttct tagtaaaatt tctactggac tgtatgtttt    420
gacaggtcag aaacatttct tcaaaagaag aacctttttgg aaactgtaca gccctttttct   480 ttcattccct ttttgctttc tgtgccaatg cctttggttc tgattgcatt atggaaaacg    540
ttgatcggaa cttgaggttt ttatttatag tgtggcttga aagcttggat agctgttgtt    600
acatgagata cctattaag tttaggccag cttgatgctt tatttttttt cctttgaagt     660
agtgagcgtt ctctggtttt tttcctttga aactggcgag gcttagattt ttctaatggg    720
attttttacc tgatgatcta gttgcatacc caaatgcttg taaatgtttt cctagttaac    780
atgttgataa cttcggattt acatgttgta tatacttgtc atctgtgttt ctagtaaaaa    840 tatatgcat ttatagaaat acgtaattcc tgatttcctt tttttttttat ctctatgctc    900 tgtgtgtaca ggtcaaacag acttcactcc tatttttatt tatagaatttt tatatgcagt   960 ctgtcgttgg ttcttgtgtt gtaaggatac agccttaaat ttcctagagc gatgctcagt   1020
aaggcgggtt gtcacatggg ttcaaatgta aaacgggcac gtttgctgct gccttcccag   1080
atccaggaca ctaaactgct tctgcaactg aggtataaat cgcttcagat cccaggaagt   1140
gtagatccac gtgcatattc ttaaagaaga atgaatactt tctaaaatat gttggcatag   1200
gaagcaagct gcatggattt atttgggact taaattattt tggtaacgga gtgcataggt   1260
tttaaacaca gttgcagcat gctaacgagt cacagcattt atgcagaagt gatgcctgtt   1320
gcagctgttt acggcactgc cttgcagtga gcattgcaga taggggtggg gtgctttgtg   1380
tcgtgttggg acacgctgcc acacagccac ctcccgaaca tatctcacct gctgggtact   1440
tttcaaacca tcttagcagt agtagatgag ttactatgaa acagagaagt tcctcagttg   1500
gatattctca tgggatgtct tttttcccat gttgggcaaa gtatgataaa gcatctctat   1560
ttgtaaatta tgcacttgtt agttcctgaa tcctttctat agcaccactt attgcagcag   1620
gtgtaggctc tggtgtggcc tgtgtctgtg cttcaatctt ttaagctt               1668
```

<210> SEQ ID NO 14
<211> LENGTH: 4672
<212> TYPE: DNA
<213> ORGANISM: Artificial Sequence
<220> FEATURE:
<223> OTHER INFORMATION: Description of Artificial Sequence: Synthetic vector

<400> SEQUENCE: 14

```
aggtcactgt gacctagatc cgcaggtcac tgtgacctac atctgatatc atcgtcgacg     60
gtatcgataa gcttcgaccg atccggcccc gcccagcgtc ttgtcattgg cgaattcgaa   120
cacgcagatg cagtcggggc ggcgcggtcc gaggtccact tcgcatatta aggtgacgcg   180
tgtggcctcg aacaccgagc gaccctgcag cgacccgctt aacagcgtca acagcgtgcc   240
gcagatctcg agagatctcg aggcatgcaa gcttggcatt ccggtactgt tggtaaaatg   300
gaagacgcca aaaacataaa gaaaggcccg gcgccattct atcctctaga ggatggaacc   360
gctggagagc aactgcataa ggctatgaag agatacgccc tggttcctgg aacaattgct   420
tttacagatg cacatatcga ggtgaacatc acgtacgcgg aatacttcga atgtccgtt    480 cggttggcag aagctatgaa acgatatggg ctgaatacaa atcacagaat cgtcgtatgc   540
agtgaaaact ctcttcaatt ctttatgccg gtgttgggcg cgttatttat cggagttgca   600
```

```
gttgcgcccg cgaacgacat ttataatgaa cgtgaattgc tcaacagtat gaacatttcg      660
cagcctaccg tagtgtttgt ttccaaaaag gggttgcaaa aaattttgaa cgtgcaaaaa      720
aaattaccaa taatccagaa aattattatc atggattcta aaacggatta ccagggattt      780
cagtcgatgt acacgttcgt cacatctcat ctacctcccg gttttaatga atacgatttt      840
gtaccagagt cctttgatcg tgacaaaaca attgcactga taatgaattc ctctggatct      900
actgggttac ctaagggtgt ggcccttccg catagaactg cctgcgtcag attctcgcat      960
gccagagatc ctattttggg caatcaaatt attccggata ctgcgatttt aagtgttgtt     1020
ccattccatc acggttttgg aatgtttact acactcggat atttgatatg tggatttcga     1080
gtcgtcttaa tgtatagatt tgaagaagag ctgttttttac gatcccttca ggattacaaa     1140
attcaaagtg cgttgctagt accaacccta ttttcattct tcgccaaaag cactctgatt     1200
gacaaatacg atttatctaa tttacacgaa attgcttctg ggggcgcacc tctttcgaaa     1260
gaagtcgggg aagcggttgc aaaacgcttc catcttccag ggatacgaca aggatatggg     1320
ctcactgaga ctacatcagc tattctgatt acacccgagg gggatgataa accgggcgcg     1380
gtcggtaaag ttgttccatt ttttgaagcg aaggttgtgg atctggatac cgggaaaacg     1440
ctgggcgtta atcagagagg cgaattatgt gtcagaggac ctatgattat gtccggttat     1500
gtaaacaatc cggaagcgac caacgccttg attgacaagg atggatggct acattctgga     1560
gacatagctt actgggacga agacgaacac ttcttcatag ttgaccgctt gaagtcttta     1620
attaaataca aaggatatca ggtggccccc gctgaattgg aatcgatatt gttacaacac     1680
cccaacatct tcgacgcggg cgtggcaggt cttcccgacg atgacgccgg tgaacttccc     1740
gccgccgttg ttgttttgga gcacggaaag acgatgacgg aaaagagat cgtggattac     1800 gtggccagtc aagtaacaac cgcgaaaaag ttgcgcggag gagttgtgtt tgtggacgaa     1860
gtaccgaaag gtcttaccgg aaaactcgac gcaagaaaaa tcagagagat cctcataaag     1920
gccaagaagg gcggaaagtc caaattgtaa aatgtaactg tattcagcga tgacgaaatt     1980
cttagctatt gtaatactgc gatgagtggc agggcgggc gtaatttttt taaggcagtt     2040
attggtgccc ttaaacgcct ggtgctacgc ctgaataagt gataataagc ggatgaatgg     2100
cagaaattcg ccggatcttt gtgaaggaac cttacttctg tggtgtgaca taattggaca     2160
aactacctac agagatttaa agctctaagg taaatataaa attttttaagt gtataatgtg     2220 ttaaactact gattctaatt gtttgtgtat tttagattcc aacctatgga actgatgaat     2280
gggagcagtg gtggaatgcc tttaatgagg aaaacctgtt ttgctcagaa gaaatgccat     2340
ctagtgatga tgaggctact gctgactctc aacattctac tcctccaaaa agaagagaa     2400 aggtagaaga ccccaaggac tttccttcag aattgctaag ttttttgagt catgctgtgt     2460
ttagtaatag aactcttgct tgctttgcta tttacaccac aaaggaaaaa gctgcactgc     2520
tatacaagaa aattatggaa aaatattctg taacctttat aagtaggcat aacagttata     2580
atcataacat actgtttttt cttactccac acaggcatag agtgtctgct attaataact     2640
atgctcaaaa attgtgtacc tttagctttt taatttgtaa aggggttaat aaggaatatt     2700
tgatgtatag tgccttgact agagatcata atcagccata ccacatttgt agaggtttta     2760
cttgctttaa aaaacctccc acacctcccc ctgaacctga aacataaaat gaatgcaatt     2820
gttgttgtta acttgtttat tgcagcttat aatggttaca aataaagcaa tagcatcaca     2880
aatttcacaa ataaagcatt ttttcactg cattctagtt gtggtttgtc caaactcatc     2940
aatgtatctt atcatgtctg gatccgtcga gggggatcca ctagttctag agcggccgcc     3000
```

```
                                                -continued accgggatcc ataatataac tgtaccaggt tttggtttat tacatgtgac tgacggcttc    3060
ctatgcgtgc tcagaaaacg gcagttgggc actgcactgc ccggtgatgg tgccacggtg    3120
gctcctgccg ccttctttga tattcactct gttgtatttc atctcttgtt gccgatgaaa    3180
ggatataaca gtctctgagg aaatacttgg tatttcttct gatcagcgtt tttataagta    3240
atgttgaata ttggataagg ctgtgtgtcc tttgtcttgg gagacaaagc ccacagcagg    3300
tggtggttgg gtggtggcag ctcagtgaca ggagaggttt ttttgcctgt ttttttttgtt   3360 gttttttttt tttaagtaag gtgttctttt ttcttagtaa aatttctact ggactgtatg    3420
ttttgacagg tcagaaacat ttcttcaaaa gaagaacctt ttggaaactg tacagccctt    3480
ttctttcatt ccctttttgc tttctgtgcc aatgcctttg gttctgattg cattatggaa    3540
aacgttgatc ggaacttgag gttttttattt atagtgtggc ttgaaagctt ggatagctgt   3600
tgttacatga gataccttat taagtttagg ccagcttgat gctttattt ttttcctttg     3660 aagtagtgag cgttctctgg ttttttttcct ttgaaactgg cgaggcttag attttttctaa  3720 tgggattttt tacctgatga tctagttgca tacccaaatg cttgtaaatg ttttcctagt    3780
taacatgttg ataacttcgg atttacatgt tgtatatact tgtcatctgt gtttctagta    3840
aaaatatatg gcatttatag aaatacgtaa ttcctgatttt ccttttttttt ttatctctat  3900 gctctgtgtg tacaggtcaa acagacttca ctcctatttt tatttataga attttatatg    3960
cagtctgtcg ttggttcttg tgttgtaagg atacagcctt aaatttccta gagcgatgct    4020
cagtaaggcg ggttgtcaca tgggttcaaa tgtaaaacgg gcacgtttgc tgctgccttc    4080
ccagatccag gacactaaac tgcttctgca actgaggtat aaatcgcttc agatcccagg    4140
aagtgtagat ccacgtgcat attccttaaag aagaatgaat actttctaaa atatgttggc   4200
ataggaagca agctgcatgg atttatttgg gacttaaatt attttggtaa cggagtgcat    4260
aggttttaaa cacagttgca gcatgctaac gagtcacagc atttatgcag aagtgatgcc    4320
tgttgcagct gtttacggca ctgccttgca gtgagcattg cagataggg tggggtgctt     4380 tgtgtcgtgt tgggacacgc tgccacacag ccacctcccg aacatatctc acctgctggg    4440
tacttttcaa accatcttag cagtagtaga tgagttacta tgaaacagag aagttcctca    4500
gttggatatt ctcatgggat gtcttttttc ccatgttggg caaagtatga taaagcatct    4560
ctatttgtaa attatgcact tgttagttcc tgaatccttt ctatagcacc acttattgca    4620
gcaggtgtag gctctggtgt ggcctgtgtc tgtgcttcaa tcttttaagc tt            4672
```